(12) United States Patent
Santiago et al.

(10) Patent No.: US 10,132,775 B2
(45) Date of Patent: *Nov. 20, 2018

(54) ENHANCED ISOTACHOPHORESIS ASSAYS USING ADDITIVES WITH SPATIAL GRADIENTS

(71) Applicants: Juan G. Santiago, Stanford, CA (US); Alexandre Persat, Metuchen, NJ (US); Giancarlo Garcia, Stanford, CA (US); Charbel Eid, Stanford, CA (US)

(72) Inventors: Juan G. Santiago, Stanford, CA (US); Alexandre Persat, Metuchen, NJ (US); Giancarlo Garcia, Stanford, CA (US); Charbel Eid, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 14/828,487

(22) Filed: Aug. 17, 2015

(65) Prior Publication Data
US 2016/0153934 A1 Jun. 2, 2016

Related U.S. Application Data

(63) Continuation of application No. 13/252,138, filed on Oct. 3, 2011, now Pat. No. 9,151,732.
(Continued)

(51) Int. Cl.
*G01N 27/447* (2006.01)

(52) U.S. Cl.
CPC ... *G01N 27/44756* (2013.01); *G01N 27/4473* (2013.01); *G01N 27/44721* (2013.01); *G01N 27/44795* (2013.01)

(58) Field of Classification Search
CPC ............ G01N 27/447; G01N 2550/00; G01N 30/86–30/8696; B01D 57/02; G06F 19/00–19/28
See application file for complete search history.

(56) References Cited

U.S. PATENT DOCUMENTS 4,790,919 A 12/1988 Baylor
8,580,097 B2 11/2013 Kurosawa et al.
(Continued)

OTHER PUBLICATIONS

Boek, Petr, et al., "Effect of a Concentration Cascade of the Leading Electrolyte on the Separation Capacity in Isotachophresis", Journal of Chromatography, 1978, pp. 323-326, vol. 156, Publisher: Elsevier Scientific Publishing Company, Published in: Amsterdam, Netherlands.
(Continued)

*Primary Examiner* — Gurpreet Kaur
(74) *Attorney, Agent, or Firm* — Eugene J. Molinelli; Beusse Wolter Sanks & Maire

(57) ABSTRACT

Techniques for enhanced isotachophoresis assays using additives with spatial gradients include forming a concentration gradient of an additive along a channel from an input port to an output port. The channel is used for isotachophoresis with ions of a leading electrolyte having a first mobility greater than a mobility of an analyte, and ions of a trailing electrolyte having a second mobility less than the mobility of the analyte. The additive is different from both the leading electrolyte and the trailing electrolyte; and the additive has a third mobility that assures the analyte will encounter the additive. The method further comprises introducing a mixture of the trailing electrolyte and a sample including the analyte. The method further comprises applying an electric field to the channel; and, measuring the analyte.

32 Claims, 16 Drawing Sheets
Specification includes a Sequence Listing.

Related U.S. Application Data

(60) Provisional application No. 61/388,921, filed on Oct. 1, 2010.

(56) References Cited

U.S. PATENT DOCUMENTS

| | | |
|---|---|---|
| 2005/0133370 A1 | 6/2005 | Park et al. |
| 2006/0042948 A1 | 3/2006 | Santiago et al. |
| 2006/0065528 A1 | 3/2006 | Lopez et al. |

OTHER PUBLICATIONS

Stover, Frederick S., "Enhancing Isotachophoresis Sensitivity by Low-Concentration Electrolyte Cascading", Journal of Chromatography, 1985, pp. 45-48, vol. 320, Publisher: Elsevier Science Publishers B.V., Published in: Amsterdam, Netherlands.

SEQUENCE LISTING

```
<160> NUMBER OF SEQ ID NOS: 13

<210> SEQ ID NO 1
<211> LENGTH: 23
<212> TYPE: RNA
<213> ORGANISM: Artificial Sequence
<220> FEATURE:
<223> OTHER INFORMATION: Synthetic oligonucleotide

<400> SEQUENCE: 1
```

-continued caaagugcuu acagugcagg uag                                      23

<210> SEQ ID NO 2
<211> LENGTH: 40
<212> TYPE: RNA
<213> ORGANISM: Artificial Sequence
<220> FEATURE:
<223> OTHER INFORMATION: Synthetic oligonucleotide

<400> SEQUENCE: 2
cugugacacu ucaaacucgu accgugagua auaaugcgcc                    40

<210> SEQ ID NO 3
<211> LENGTH: 60
<212> TYPE: RNA
<213> ORGANISM: Artificial Sequence
<220> FEATURE:
<223> OTHER INFORMATION: Synthetic oligonucleotide

<400> SEQUENCE: 3
cauuauuacu uuggua cgc gcugugacac uucaaacucg uaccgugagu aauaaugcgc    60

<210> SEQ ID NO 4
<211> LENGTH: 22
<212> TYPE: RNA
<213> ORGANISM: Artificial Sequence
<220> FEATURE:
<223> OTHER INFORMATION: Synthetic oligonucleotide: miR-126

<400> SEQUENCE: 4
ucguaccgug aguaauaaug cg                                       22

<210> SEQ ID NO 5
<211> LENGTH: 22
<212> TYPE: RNA
<213> ORGANISM: Artificial Sequence
<220> FEATURE:
<223> OTHER INFORMATION: Synthetic oligonucleotide: complimentary to
    miR-126

<400> SEQUENCE: 5
cgcauuauua cucacgguac ga                                       22

<210> SEQ ID NO 6
<211> LENGTH: 22
<212> TYPE: RNA
<213> ORGANISM: Artificial Sequence
<220> FEATURE:
<223> OTHER INFORMATION: Synthetic oligonucleotide: miR-26a

<400> SEQUENCE: 6
uucaaguaau ccaggauagg cu                                       22

<210> SEQ ID NO 7
<211> LENGTH: 22
<212> TYPE: RNA
<213> ORGANISM: Artificial Sequence
<220> FEATURE:
<223> OTHER INFORMATION: Synthetic oligonucleotide: miR-122

<400> SEQUENCE: 7
uggaguguga caauggu guu ug                                      22

<210> SEQ ID NO 8
<211> LENGTH: 77

-continued

```
<212> TYPE: RNA
<213> ORGANISM: Artificial Sequence
<220> FEATURE:
<223> OTHER INFORMATION: Synthetic oligonucleotide: mir-26a

<400> SEQUENCE: 8
guggccucgu ucaaguaauc caggauaggc ugugcagguc ccaaugggcc uauucuuggu    60
uacuugcacg gggacgc                                                   77

<210> SEQ ID NO 9
<211> LENGTH: 34
<212> TYPE: DNA
<213> ORGANISM: Artificial Sequence
<220> FEATURE:
<223> OTHER INFORMATION: Synthetic oligonucleotide: miR-26a MB
<220> FEATURE:
<221> NAME/KEY: misc_feature
<223> OTHER INFORMATION: Fluorophore TYE665 on 5' end and Iowa Black RQ
      (IBRQ) on 3' end

<400> SEQUENCE: 9
ccgagcagcc tatcctggat tacttgaagc tcgg                                34

<210> SEQ ID NO 10
<211> LENGTH: 34
<212> TYPE: DNA
<213> ORGANISM: Artificial Sequence
<220> FEATURE:
<223> OTHER INFORMATION: Synthetic oligonucleotide: miR-122 MB
<220> FEATURE:
<221> NAME/KEY: misc_feature
<223> OTHER INFORMATION: Fluorophore TYE665 on 5' end and Iowa Black RQ
      (IBRQ) on 3' end

<400> SEQUENCE: 10
ccgagccaaa caccattgtc acactccagc tcgg                                34

<210> SEQ ID NO 11
<211> LENGTH: 22
<212> TYPE: RNA
<213> ORGANISM: Artificial Sequence
<220> FEATURE:
<223> OTHER INFORMATION: Synthetic oligonucleotide: miR-15a

<400> SEQUENCE: 11
uagcagcaca uaaugguuug ug                                             22

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide: miR-15a Probe
<220> FEATURE:
<221> NAME/KEY: misc_feature
<223> OTHER INFORMATION: Acrydite on 5' end

<400> SEQUENCE: 12
gtagcagcac ataatggttt gtg                                            23

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide: miR-15a Reporter
<220> FEATURE:
<221> NAME/KEY: misc_feature
```

```
<223> OTHER INFORMATION: Cy3 on 5' end

<400> SEQUENCE: 13
cacaaaccat tatgtgctgc ta                                              22
```

ENHANCED ISOTACHOPHORESIS ASSAYS USING ADDITIVES WITH SPATIAL GRADIENTS

CROSS-REFERENCE TO RELATED APPLICATIONS

This application claims benefit as a Continuation of application Ser. No. 13/252,138, filed Oct. 3, 2011, the entire contents of which are hereby incorporated by reference as if fully set forth herein, under 35 U.S.C. § 120; which claims benefit of Provisional Appln. 61/388,921, filed Oct. 1, 2010, the entire contents of which are hereby incorporated by reference as if fully set forth herein, under 35 U.S.C. § 119(e).

STATEMENT OF GOVERNMENTAL INTEREST

This invention was made with Government support under contract N66001-09-C-2082 awarded by the Defense Advanced Research Projects Agency and under contract TR000093 awarded by the National Institutes of Health. The Government has certain rights in the invention.

BACKGROUND OF THE INVENTION

Isotachophoresis (ITP) separates charged molecules (ions) in a sample based on their different effective mobility. Effective mobility is the proportionality constant between observable drift velocity of an ion and applied electric field. It is a function of ion shape, size, and the degree of ionization.

ITP uses a leading electrolyte (LE) which contains a relatively high mobility ion, and a trailing electrolyte (TE) with a relatively low mobility ion. The TE and LE ions are chosen to have effective mobilities respectively lower and higher than target analyte ions of interest. That is, the effective mobility of analyte ions is higher than that of the TE and lower than that of the LE. These target analytes have the same sign of charge as the LE and TE ions (i.e., a co-ion). An applied electric field causes LE ions to move away from TE ions and TE ions to trail behind. A moving interface forms between the adjacent and contiguous TE and LE zones. This creates a region of electric field gradient (typically from the low electric field of the LE to the high electric field of the TE). Analyte ions in the TE overtake TE ions but cannot overtake LE ions and accumulate ("focus") at the interface between TE and LE. Alternately, target ions in the LE are overtaken by the LE ions; and also accumulate at interface.

SUMMARY OF THE INVENTION

Techniques are provided for enhanced ITP assays using additives with spatial gradients.

According to a first set of embodiments, a method includes forming a concentration gradient of an additive along a channel from an input port to an output port. The channel is used for isotachophoresis with ions of a leading electrolyte having a first effective mobility magnitude greater than a mobility of an analyte, and ions of a trailing electrolyte having a second effective mobility magnitude less than the mobility of the analyte. The additive is different from both the leading electrolyte and the trailing electrolyte; and the additive has a third effective mobility that assures the analyte will encounter the additive. The method further comprises contacting a sample including the analyte to the leading electrolyte and contacting the trailing electrolyte to the sample. The method further comprises applying an electric field to the channel; and, measuring the analyte.

An additive has a mobility that assures the analyte will encounter the additive when: the additive has a (signed) effective mobility greater than that of the TE in the case of anionic ITP; or, the additive has a (signed) effective mobility less than that of TE in the case of cationic ITP. As used herein, measuring the analyte includes detecting, quantifying, collecting, extracting and otherwise using the analyte.

According to various other sets of embodiments, an apparatus comprises means to perform each step of at least one of the above methods.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1A:
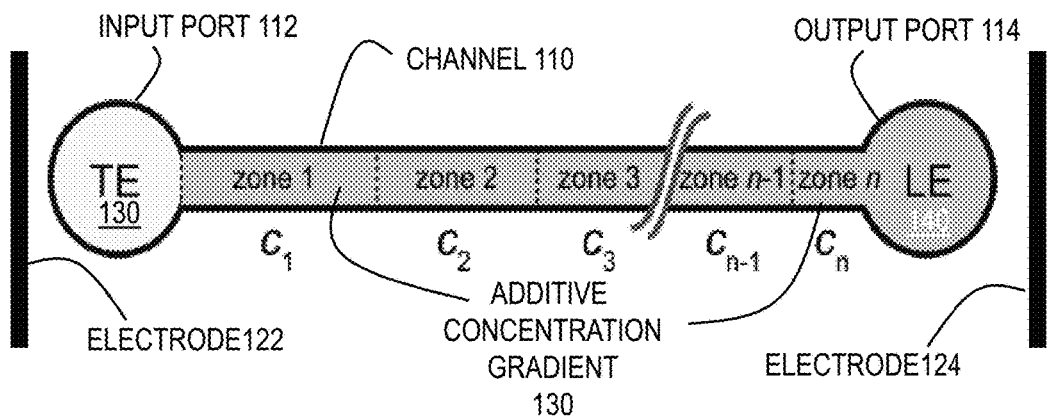
FIG. 1A is a diagram that illustrates an example isotachophoresis channel with a spatial gradient of an additive prior to application of an external electric field, according to an embodiment.

A method and apparatus are described for enhanced isotachophoresis assays using additives with spatial gradients. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of separating then detecting microRNA in a mixture with larger RNA strands, for example, as found in cellular material, using a microchannel. However, the invention is not limited to this context. In other embodiments the same or different analyte is separated for purification or detection or some other activity in microchannels or larger or smaller channels. The proposed methods bring a substantial gain in flexibility or speed over traditional isotachophoresis approaches.

As used herein, an analyte is any collection of one or more kinds of ions that is targeted for separation from other species. Example analytes include microRNA (miRNA), small interfering RNA, ribosomal RNA, messenger RNA, genomic DNA, proteins of interest, or small organic or inorganic molecules. Deoxyribonucleic acid (DNA) is a usually double-stranded long molecule that encodes other shorter molecules, such as proteins, used to build and control all living organisms. DNA is composed of repeating chemical units known as "nucleotides" or "bases." There are four bases: adenine, thymine, cytosine, and guanine, represented by the letters A, T, C and G, respectively. Adenine on one strand of DNA always binds to thymine on the other strand of DNA; and guanine on one strand always binds to cytosine on the other strand and such bonds are called base pairs. Any order of A, T, C and G is allowed on one strand, and that order determines the complementary order on the other strand. The actual order determines the function of that portion of the DNA molecule. Information on a portion of one strand of DNA can be captured by ribonucleic acid (RNA) that also comprises a chain of nucleotides in which uracil (U) replaces thymine (T). Determining the order, or sequence, of bases on one strand of DNA or RNA is called sequencing. A portion of length k bases of a strand is called a k-mer; and specific short k-mers are called oligonucleotides or oligomers or "oligos" for short. The term nucleic acid is used herein to refer to any DNA molecule or RNA molecule or multi-nucleotide fragment or mixture thereof, whether a oligo or not.

A microfluidic channel, also called a micro channel herein, is a channel for fluid flow with a width and height each less than 1000 microns (1 micron=1 micrometer, μm, $=10^{-6}$ meters). Microchannels can be etched in borosilicate glass using standard microfabrication processes. Microchannels can also be fabricated in fused silica, acrylic, polycarbonate, or polydimethylsiloxane.

As used herein, the leading electrolyte (LE) refers to the high effective mobility co-ions rather than all constituents of a solution in the channel before introduction of a sample and the trailing electrolyte. Similarly, the trailing electrolyte (TE) refers to the low effective mobility co-ions rather than the constituents of the sample or other constituents of the solution in the channel after the interface with the LE has passed.

An additive is a molecule different from both the leading electrolyte (LE) and the trailing electrolyte (TE); and the additive has a third effective mobility that assures the analyte will encounter the additive. The additive can be positively charged, negatively charged, variably charged or electrically neutral. The spatial gradient of the additive refers to a non-zero change in concentration of the additive along the length of the channel; and, the gradient can be positive, negative, constant or variable, e.g., ranging among positive, zero and negative values.

1. Overview

In this section, an overview of the methods and apparati are given. More detailed embodiments are described in later sections. One section presents some detailed embodiments for quantification of microRNA content in a sample which also includes unwanted longer RNA strands, as found for example in cellular material, or, more specifically, the total RNA content of a cell. Another section presents embodiments in which the microRNA is extracted using additive gradients and then hybridized with molecular beacons that fluoresce when particular sequences of nucleotide bases are encountered. In other embodiments, different methods are used to introduce gradients in one or more additives, or reporters such as molecular beacons bound to the analyte are separated from such reporters that are not bound to the analyte by varying the properties of a polymer sieve or by introducing spacer ions or both. Below, references are cited, each of which is hereby incorporated by reference as if fully set forth herein, except so far as the terminology is inconsistent with the terminology used herein.

The additive can be used to perform any function during isotachophoresis, including preferentially entangling long molecules, preventing or encouraging folding (e.g., secondary and tertiary structures) of molecules, or labeling molecules with one or more fluorophores, among many others. Because of the spatial gradient, the function of the additive is performed to greater or lesser degree at different locations along the channel, depending on the concentration of the additive at that location.

By virtue of the effective mobility of the additive by definition, the analyte sequentially moves through the different concentrations of the additive as the analyte moves along the channel during isotachophoresis. Thus, the analyte experiences the functions of the additive corresponding to the additive's concentration in sequence as the analyte moves through the channel. The ITP channel becomes like an assembly line to process a sample with a sequence of operations.

FIG. 1A is a diagram that illustrates an example isotachophoresis channel 110 with a spatial gradient of an additive before application of an external electric field, according to an embodiment. The channel 110 connects an input port 112 to an output port 114 and is disposed between two electrodes 122 and 124. Before an external electric field is applied between the electrodes, the channel and output port 114 are filled with the LE mixed with one or more additives.

According to various embodiments, the concentration of one or more additives changes along the length of the channel, either continuously or abruptly, thus setting up a spatial gradient of additive concentration. Any method may be used to establish the spatial gradient, such as sequentially introducing different mixtures of LE and additive through the input port 112, or introducing different concentrations of additive or additive and LE mix through side ports (not shown) distributed along the channel 110, or by differentially polymerizing monomers or short polymers, among other approaches. The spatially non-uniform concentrations of additives are represented in FIG. 1A by zone 1 though zone n with corresponding additive concentrations C1 through Cn, called the additive concentration gradient 130, hereinafter. In various embodiments, the concentrations of various additives increase or decrease with distance or both, so, in some embodiments, the concentration gradient is neither constant nor monotonic. In some embodiments, each zone is relatively homogenous with discrete concentrations of one or more additives and sharp additive concentration changes at zone boundaries. In some embodiments, the spatial gradient in the channel is smooth and slowly changing and each zone has a range of concentrations of one or more additives without sharp additive concentration discontinuities at the zone boundaries.

Any additive that provides a useful function during ITP may be used in various embodiments. An example additive is a polymer sieving matrix (e.g. for the sieving of nucleic acids) such as polyvinylpyrrolidone, polyethylene glycol, polyethylene glycol, hydroxyethyl cellulose, poly(N,N-dimethylacrylamide), pluronic F127, agarose, linear polyacrylamide, acrylamide etc. Another example additive is a denaturing agent (e.g. for preventing secondary structures of nucleic acids, such as folding and hybridizing to a second strand, which interferes with sieving) such as formamide, urea, N,N-dimethylformamide, acetic acid, guanidinium chloride etc. a surfactant such as Triton X-100, Triton X-200, Tween 20, Tween 80, saponin (e.g. for cell lysis). Another example additive is a fluorophore, such as rhodamine B, rhodamine 123, rhodamine 6G, fluorescein dyes, Alexa Fluor dyes, Cy dyes, Bodipy dyes, DyLight dyes, green fluorescent protein, red fluorescent protein. Another example additive is a labeled probe such as molecular beacons, Taqman, oligonucleotide probe end-labeled with a fluorophore and, in some embodiments, a fluorescence quencher at the other end. Another example additive is acrylamide-modified oligo (e.g., 5' modification Acrydite). As used herein, a reporter is any molecule that binds to an analyte to make the analyte more detectable. Reporters include a fluorophore, a quantum dot, and labeled probes, among others. Another example additive is a reagent for interacting with the segregated or bound analyte.

Figure 1B:
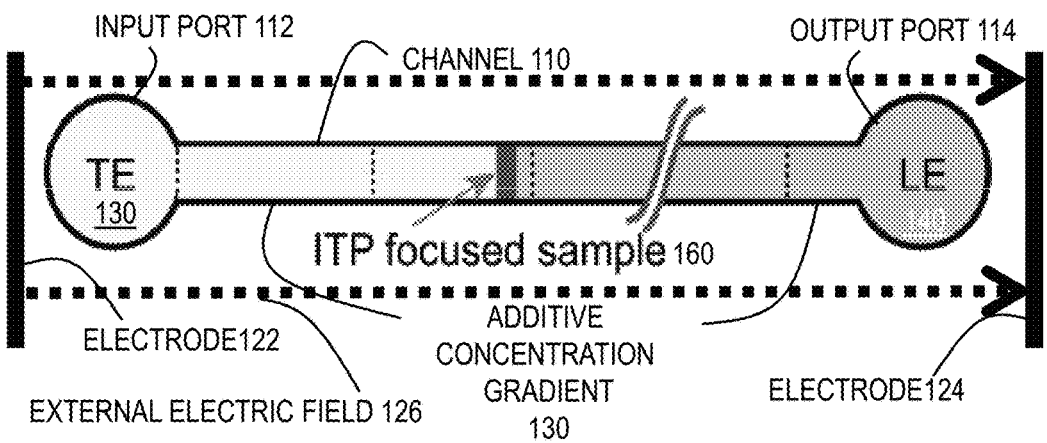
FIG. 1B is a diagram that illustrates an example isotachophoresis channel with a spatial gradient of an additive after application of an external electric field, according to an embodiment.

FIG. 1B is a diagram that illustrates an example isotachophoresis channel with a spatial gradient of an additive after application of an external electric field, according to an embodiment. Upon application of the external electric field 126 (shown in the direction of the moving ions), the target analytes of the sample 160 focus at the LE-TE interface and propagate through the sequence of relatively stationary zones, from left to right. In some following illustrations, the electric field direction is depicted as directed from positive charge to negative charge and is therefore directed opposite to the direction of flow of the ions, e.g., for negatively charged ions (anions).

Figure 1C:
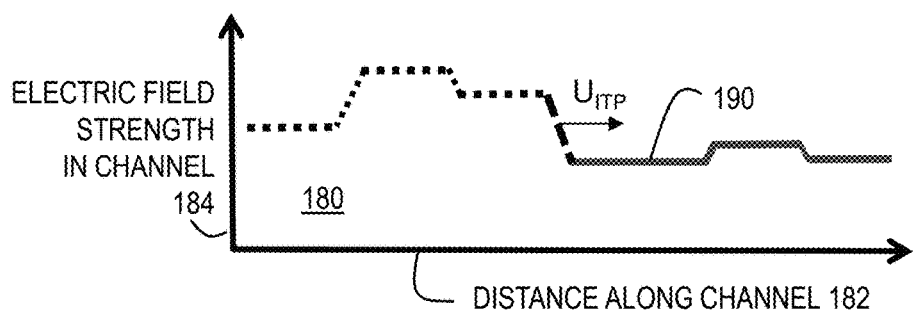
FIG. 1C is a graph that illustrates an example electric field in the channel at a time that corresponds to FIG. 1B.

FIG. 1C is a graph 180 that illustrates an example electric field 190 in the channel at a time that corresponds to FIG. 1B. The horizontal axis 182 is distance along the channel (relative units); and the vertical axis 184 is electric field in the channel (relative units). The mobility of the TE is less than the mobility of the LE, so the conductivity and the electric field strength in the TE are, respectively, lower and higher than those of the LE. A steep electric field gradient (dashed line) is created at the ITP interface traveling at velocity $U_{ITP}$ between TE (dotted line) and LE (solid line); other electric field gradients in the channel are created by the difference in conductivities of additives in discrete zones. A target analyte ion in the sample which encounters the higher electric field of the TE, speeds up and focuses at the interface. Similarly, a target analyte ion in the sample which encounters the lower electric field of the LE, slows down and returns to the focus at the interface as this interface propagates from left to right.

As the analyte encounters each additive concentration zone, the analyte interacts with the additives in that zone according to the effect of the concentration of the additive in the encountered zone. Thus, each additive operates most effectively on a component of the sample along a portion of the channel where the concentration of the additive is in a particular range of concentrations.

In some embodiments, the channel is a microchannel.

2 Apparatus

Figure 2A:
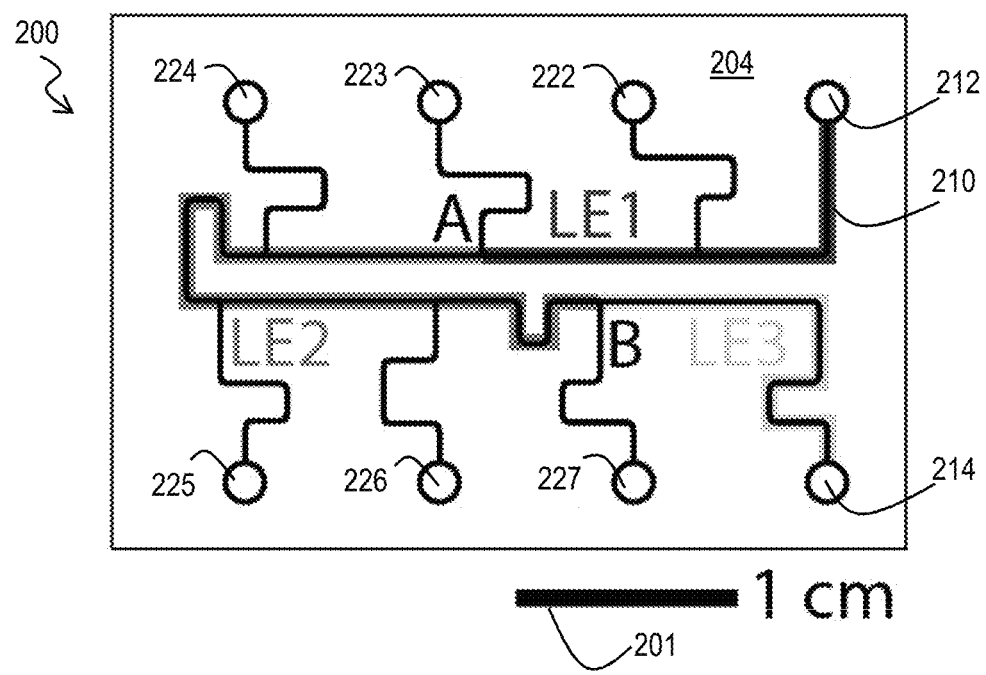
FIG. 2A is a block diagram that illustrates an example isotachophoresis channel formed in a glass substrate, according to an embodiment.

FIG. 2A is a block diagram that illustrates an example isotachophoresis channel 210 formed in a glass substrate, according to an embodiment. At least some experiments described below were performed in an off-the-shelf borosilicate glass microfluidic chip (model NS260, Caliper LS, Mountain View, Calif.) depicted in FIG. 2. A scale bar 201 indicates a length scale of 1 centimeter (cm, $1\ cm=10^{-2}$ meters). The channel 210 connects an input port 212 to output (exit) port 214. Along the channel, six reservoir ports 222, 223, 224, 225, 226, 227 are connected to the channel at corresponding T-junctions. Each reservoir is cylindrical 1.8 mm in diameter and 1 mm in depth. The reservoir ports (collectively referenced hereinafter as reservoir ports 220) are each connected to channel 210 by 12 micron deep, 44 micron wide wet-etched borosilicate glass microchannels. These reservoir ports allow for forming multiple zones of additive concentrations. For example, three additive concentration zones are provided in some embodiments described below by contacting a first additive mixture with the LE (designated mixture LE1) at ports 212, 222, 223 up to point A, and contacting a second additive mixture with the LE (designated mixture LE2) at ports 224, 225, 226 up to point B, and contacting a third additive mixture with the LE (designated mixture LE3) at ports 222, 214 up to the output port. Means for establishing particular concentration gradients of particular additives are described in more detail below with reference to various embodiments.

Figure 2B:
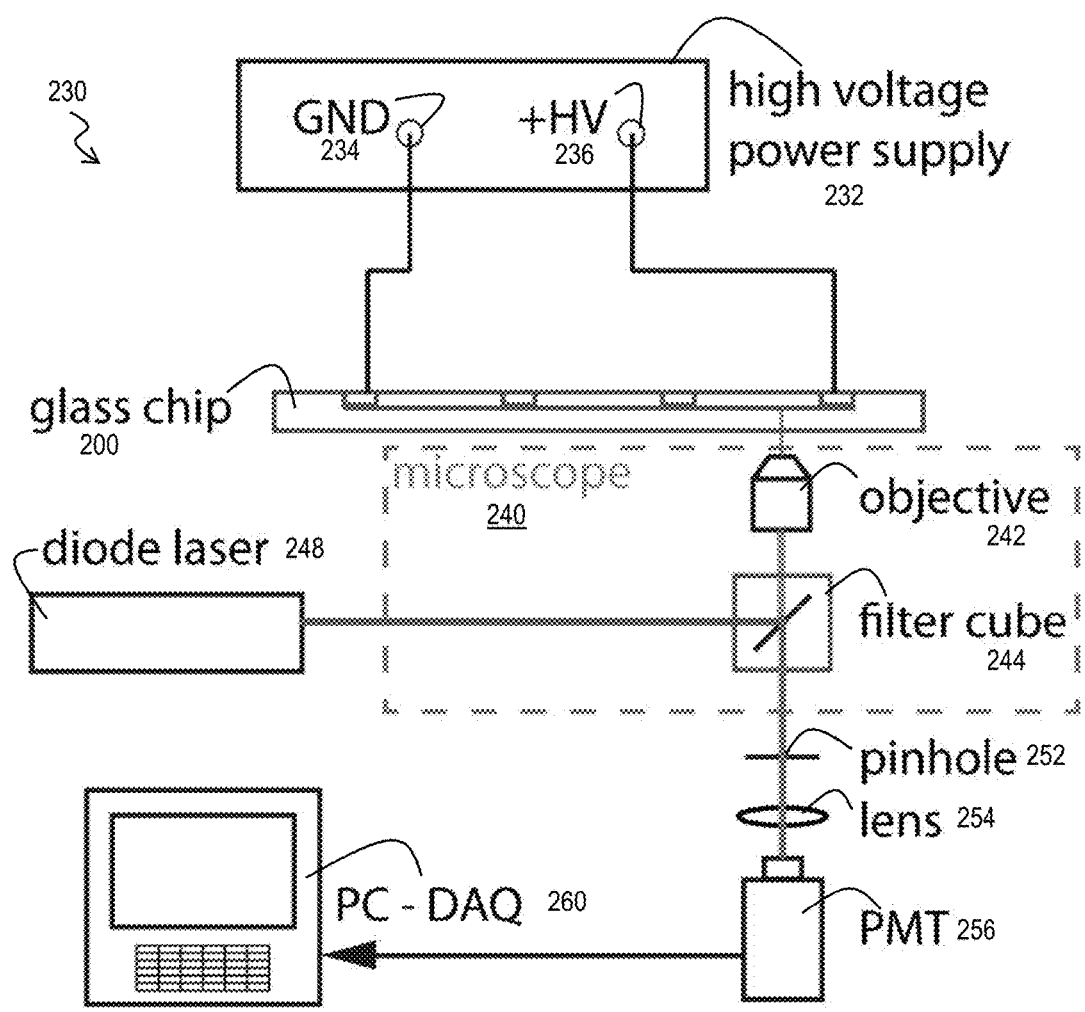
FIG. 2B is a block diagram that illustrates an example apparatus for measuring analyte using an isotachophoresis channel formed in a glass substrate, according to an embodiment.

FIG. 2B is a block diagram that illustrates an example apparatus 230 for measuring analyte using an isotachophoresis channel formed in a glass substrate, according to an embodiment. Besides the glass chip 200 depicted in FIG. 2A, the apparatus 230 includes a high voltage power supply 232 having an electrical ground (GND) terminal 234 and a selectable voltage at a high voltage (HV) terminal 236. The apparatus further includes microscope 240 with an objective lens 242 and optical filter cube 244, a diode laser 248, optical detection including a pinhole 252, lens 254 and photomultiplier tube (PMT) 256. PMT data were digitized and processed in a computer, such as PC-DAQ 260, described below.

For example, in some experimental embodiments, fluorescence data was acquired using an inverted epifluorescence microscope 240 model Eclipse TE200 from Nikon of Japan, equipped with a laser diode illumination 248 (642 nanometer, nm, wavelength, $1\ nm=10^{-9}$ meters) model Stradus 642 from Vortran of Sacramento, Calif. Light was filtered using a standard Cy5 cube 244 (exciter/emitter 630/695 nm) model XF110-2 from Omega Optical of Brattleboro, Vt., and focused though a 60× water immersion objective 242 (N.A.=1.0) model Fluor from Nikon of Japan. To reduce noise from out of focus light sources in the returned fluorescent light, a custom confocal assembly was built by placing a 150 micron diameter pinhole provided as a mounted precision pinhole from Edmund Optics of Barrington, N.J. at the image focal plane. Fluorescence intensity was measured using a lens 254 and PMT 256 model H7422-40 from Hamamatsu Photonics of Japan, with voltage set to 900 volts (V). The PMT signal was converted using an amplifier/converter unit model C7319 from Hamamatsu of Japan, and was filtered with a simple low pass RC circuit (RC=1.2 ms). The resulting voltage signal was acquired at personal computer 260 with a DAQ card model NI USB-6211 from National Instruments of Austin, Tex. controlled with Matlab software from The Mathworks of Natick, Mass. In some experimental embodiments, measurements were collected at 250 kilo-samples per second (kS/s, $1\ kS/s=10^{3}$ samples per second) data rate; and, a 4,000 points moving average was applied to the signal for analysis. In some embodiments measurements are performed at 90 kS/s and filtered with a 1500 point moving average. In some embodiments, to characterize a fluorescence peak, the voltage trace was analyzed by fitting a Gaussian function to the ITP peak. Fluorescence intensity was then calculated by integrating the raw data under the fit over three standard deviations.

To produce the temporally changing spatial profiles (spatiotemporal plots) in some embodiments, a mercury lamp is used for illumination in lieu of diode laser 248, with blue/green filter (Omega XF115-2) as filter 244, 4× objective lens as objective 242, and Princeton Instruments Coolsnap charge coupled device (CCD) camera to image a length of the channel in lieu of pMT 256. Winview32 software was used to control the camera from a PC. In some embodiments, a 488 nm collimated diode light source from Thorlabs of Newton, N.J. was used for illumination, in lieu of diode laser 248. A 4× objective lens (N.A.=0.2) model Plan Apo from Nikon of Japan was used as objective 242. Images along a length of the channel were acquired using a cooled CCD camera model Cascade 512F from Photometrics of Tucson, Ariz. controlled with Winview32 software from Princeton Instruments of Trenton, N.J. operating on PC 260 in lieu of PMT 256.

3 Method

Figure 3:
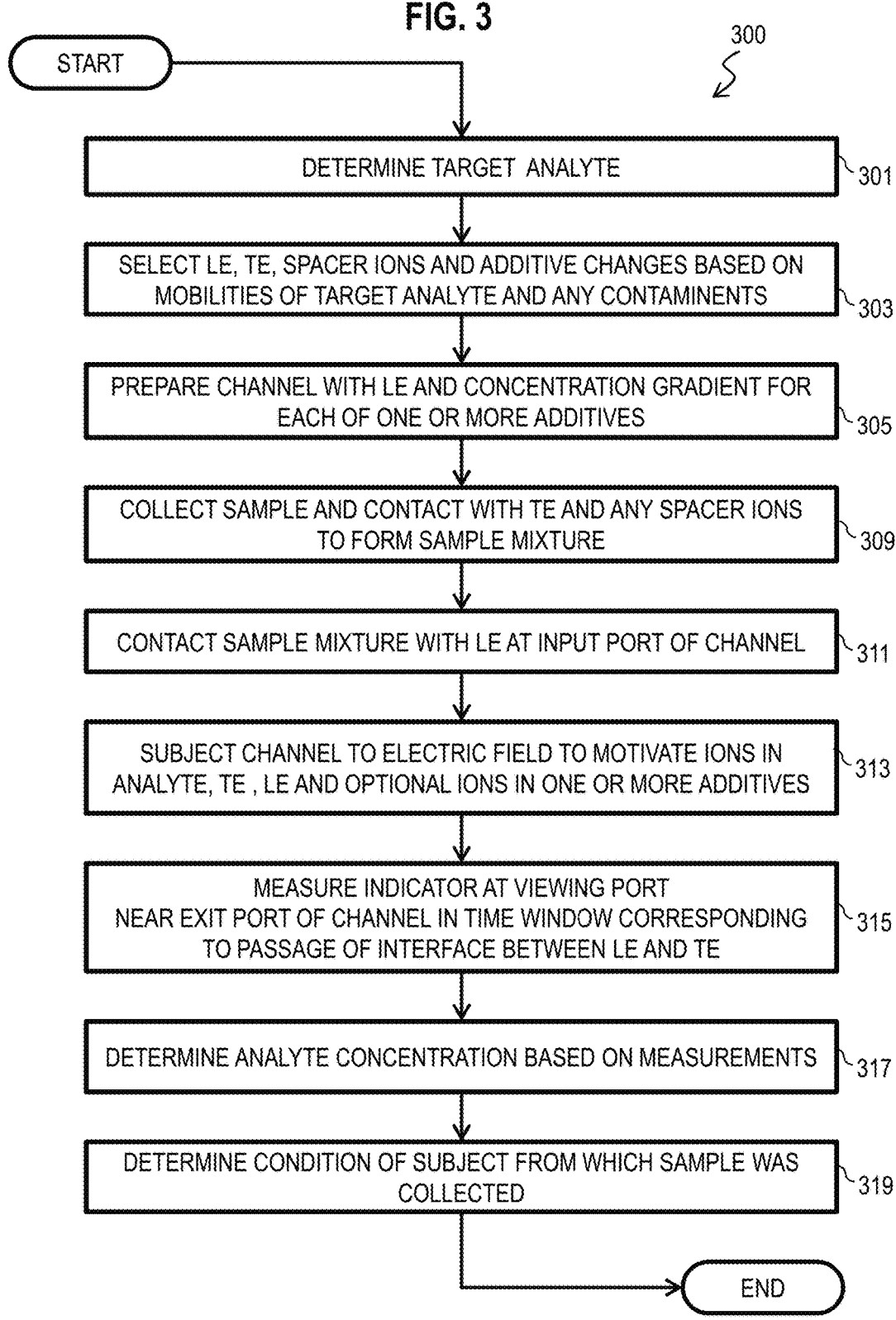
FIG. 3 is a flow diagram that illustrates an example method for performing isotachophoresis with gradients in an additive, according to an embodiment.

FIG. 3 is a flow diagram that illustrates an example method 300 for performing isotachophoresis with gradients in an additive, according to an embodiment. Although steps are depicted in FIG. 3 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 301, the analyte to be measured is determined. For example, in some embodiments, the analyte is a microRNA (miRNA) molecule, with on the order of ten nucleotides, or a miRNA molecule including a particular sequence of nucleotides, as described for various embodiments in more detail below.

In step 303 the TE, LE, spacer ions, and one or more additive gradients are selected based on the relative motilities of the analyte and any contaminants to be separated from the analyte. For example, in the illustrated embodiments, analyte miRNA is separated from long RNA contaminants, or is separated from miRNA with incorrect sequences that are regarded as contaminants. In some embodiments, spacer ions are used, as described in more detail below. In some embodiments, spacer ions are used, as described in more detail below. Spacer ions are described in United States Published Patent Application US-2010-0084271-A1, published on Apr. 8, 2010, the entire contents of which are hereby incorporated by reference as if fully set forth herein, except as the terminology used therein is not consistent with the terminology used herein. Spacer ions are selected to have a mobility that is between the mobilities of one or more molecules that react (reactants) and the mobility of a product molecule of those reactants. For example, spacer ions are used to separate a miRNA molecule and a probe specific to a particular sequence of nucleotides, from the hybrid of the probe with an miRNA molecule that matches the particular sequence, as described in more detail below.

Additives are selected to prepare the analyte for measurement, e.g., reporters, including sequence specific probes, denaturants to reduce secondary structure, enzymes to foster interaction, accelerators that increase rate of hybridization, polymers or gels to slow the movement of longer molecules, reactants to form or condition the analyte, among others. Additive mobility is selected to ensure that the analyte will be exposed to the additive gradient during the transit of the analyte from input port to output port.

In step 305, the channel is prepared for initial concentrations of the LE and one or more additive gradients. For example, various mixtures are contacted to the reservoir ports 220 of glass chip 200. In some embodiments, step 305 includes differentially polymerizing a monomer or small polymers, or both, along the channel, as described in more detail in a later section. The differential polymerization causes differences in cross-linking and forms a gel fixed to one or more channel walls differentially along the length of the channel. In some embodiments with polymerized gels, a surface modification is applied to the microchannel prior during step 305 before introducing the one or more mixtures. For example, in some embodiments, the channel is coated with 3-(trimethoxysilyl)propyl methacrylate. With this coating in place, after polymerization, the gel becomes covalently bound to the channel surface, which prevents the gel from slipping in the channel (e.g. due to electro-osmotic flow, or shrinking).

In step 309, a sample containing analyte or analyte precursor is collected and prepared and contacted to the TE and any spacer ions to form a sample mixture. In step 311, the sample mixture is contacted to the input port of the channel, e.g., 112 or 212. In some embodiments, steps 309 and 311 are performed together, and the sample mixture is formed at the input port 112 or 212.

In step 313 the channel is subjected to an electric field to motivate ions in the channel. For example, external electrodes are charged in some embodiments. In some embodiments, an electrode inside the input port is electrically grounded and an electrode in the output port is charged to a high voltage.

In step 315, an indicator of the analyte is measured at a viewing point near the output (exit) port of the channel during a time window that corresponds to the passage of the analyte. In some embodiments, the measurements are made for a longer duration to measure conditions before and after the passage of the analyte. In some embodiments, the viewing port is moved along the channel, either by motion of the microscope 240 or by motion of the glass chip 200 or some combination. The indicator is any measurable that is related to the concentration or state of the analyte, such as fluorescent emissions from a reporter or from the analyte itself. In various embodiments the indicator is optical transmission, absorption, spectra thereof, magnetic signal, voltage, among others.

In step 317, the presence/concentration of the analyte is determined based on the measurements. For example, an area under a measured fluorescence peak is converted to analyte concentration based on calibration curves formed by performing steps 305 to 315 with samples having known concentrations of analyte).

In step 319, the condition of a subject from which the sample was taken is determined based on the presence/concentration of the analyte. For example, the subject is determined to have abnormal liver function based on miRNA sequences that are not normal for liver cells. For example, a sample of nucleic acids extracted from blood or urine of the subject is determined to have show presence/absence of a pathogen (bacterial or viral) or toxin, e.g., diagnosing urinary tract infections based on detecting *e. coli* rRNA using molecular beacon.

Method 300 provides an assay for the detection and quantification of analytes, such as miRNA targets in total RNA samples. The assay is based on an ITP process which selectively focuses and accentuates detection of analyte, e.g., via hybridizations with molecular beacons (MB). In some embodiments, described in more detail in the next section, ITP hybridization is a fast (<2 minute), low component cost (about $50 per chip, standard epifluorescence microscope and power supply, about $0.50 of reagents per 100 runs), and sensitive (down to 3,000 copies per cell) microfluidic method for miRNA profiling that requires small amounts of sample (100 nanograms, ng, 1 ng=$10^{-9}$ grams, of total RNA) with about three decade dynamic range. Its speed, automation and low sample consumption make it an attractive alternative to PCR or northern blot analysis. It is anticipated that further optimization of ITP and MB chemistries and dynamics would significantly enhance sensitivity and reach the 100 copies per cell level. It is also anticipated that ITP hybridization can be extended to the detection and quantification of any type of nucleic acids, for example messenger, ribosomal RNA or genomic DNA. This has been shown in a recent publication, see Bercovici et al., Analytical Chemistry 2011 for work on diagnosing urinary tract infections based on detecting *e. coli* rRNA using molecular beacon 4. Example Embodiments 4.1 Polymer Gel Additive In some embodiments, discrete gel sieving matrix concentration gradients are used to separate analytes, thus coupling isotachophoresis (ITP) with spatially varying capillary gel electrophoresis (CGE). Ultraviolet (UV) light is used to create a discrete gel region within a microchannel, thus partitioning the channel longitudinally into two zones. In some embodiments, long polymers in solution serve as the sieving matrix. In the embodiments described here, however, a gel polymerized in place can form more and stronger cross-links and become fixed to one or more walls of the channel to form a sieving matrix that is fixed and abruptly changing with distance along the channel. By using photolithography techniques, the gel can be formed along any arbitrary portion of a microchannel.

In a first zone, analytes in free solution focus in peak mode ITP, resulting in a single sharp peak. Upon entering the gel (sieving matrix) region, analyte mobility decreases below TE mobility. Analytes therefore separate according to their effective mobilities within this region. Separation relies on significant retardation of large molecules (e.g. DNA) as compared to small ions (e.g. TE and LE ions). These interactions are dependent on several factors, including analyte structure and size. This technique is demonstrated by separating a double stranded DNA ladder containing oligonucleotides ranging from 100 nucleotides (nt) to 12,000 nt in a 6% polyacrylamide gel matrix.

Figure 4A:
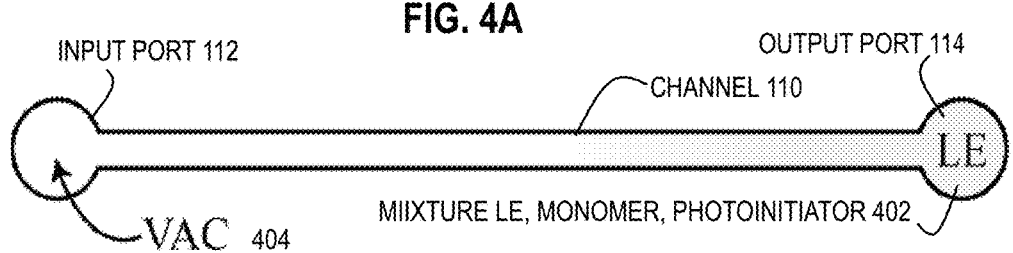
FIG. 4A through FIG. 4D are block diagrams that illustrate example arrangements of an example isotachophoresis channel after steps of an example method for performing isotachophoresis with gradients in an additive, according to an embodiment.
Figure 4B:
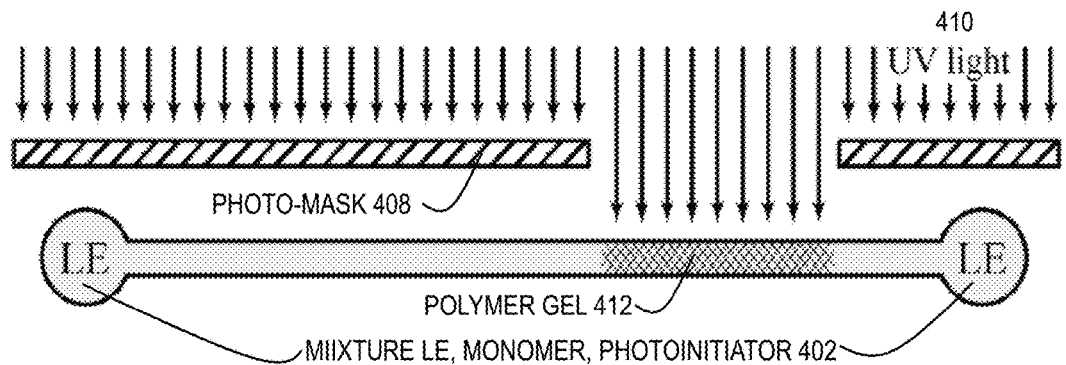

FIG. 4A through FIG. 4D are block diagrams that illustrate example arrangements of an example isotachophoresis channel after steps of an example method for performing isotachophoresis with gradients in a gel additive, according to an embodiment. FIG. 4A and FIG. 4B show arrangement of channel 110 during portions of channel preparation step 305 of method 300. In FIG. 4A, the channel 110 is filled from the output port 114 with a mixture 402 comprising a buffer that contains the leading electrolyte (LE), acrylamide/bisacrylamide monomer and a cross-linker, and a photo-initiator. In an experimental embodiment, the following was used:—50 mM Hydrochloric Acid (HCl) as LE,—100 mM Tris as a counterion,—6% (w/v) acrylamide as monomer—3.3% (w/w) bisacrylamide as crosslinker—0.2% (w/v) VA-086 as a photoinitiator. The channel 110 is filled with the help of a vacuum 404 contacted to input port 112.

In FIG. 4B, a photo-mask 408 is used to cover portions of the channel 110, allowing spatially-selective exposure to polymerizing light, e.g., UV light 410, thus photo-patterning a desired portion with fine spatial resolution and an abrupt boundary. As a result of the polymerization, a polymer gel 412 is fixed in the channel 110. Although this example polymerizes a monomer with UV light, in other embodiments the gel is polymerized in place using other cross-linkers, polymerization initiators and polymerizing energy (e.g., heat, visible light, among others). In an experimental embodiment, the channel was illuminated for a period of 6 minutes and a distance of 1.5 cm using a mercury lamp with a 50:50 beam-splitter. The intensity of the UV light is 300 mW/cm$^2$ over a uniform beam area of 0.28 cm$^2$.

Figure 4C:
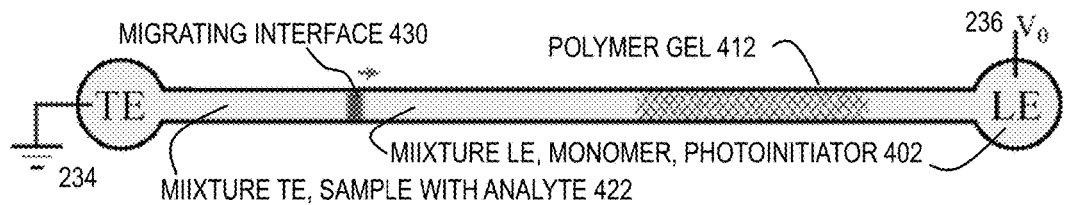
Figure 4D:
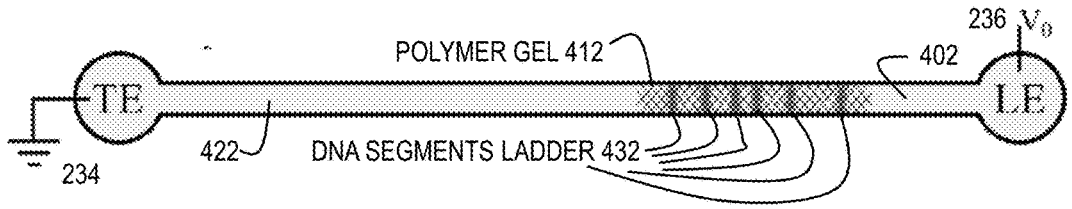

In step 311, a buffer containing the trailing electrolyte (TE) and the conditioned (e.g., fluorescently-labeled) analytes or intercalating dye of choice are added to one of the wells, e.g., to input port 112, replacing and contacting the LE buffer. In step 313, an electric field is applied using electrodes 236, 234 in the wells. ITP is thus carried out. As shown in FIG. 4C, ITP focuses the analytes in a migrating interface 430 between the fast LE ions in mixture 402 and the slow TE ions in buffer 422. The formation of a single focused peak is observed as the analytes approach the region with the polymer gel 412. FIG. 4D depicts the separation of the DNA molecules by size in the polymer gel. Upon entrance in the region of the polymer gel 412, the rapid resolving of the focused peak into multiple, lower intensity bands 432 is observed, indicating successful separation of different size oligonucleotides through CGE. This separation is a result of the analytes' interactions with the gel, which has a more significant retardation effect on larger DNA. This allows the TE, an ion, which is not retarded by the gel to the same extent, to progressively pass these bands, thus separating them. Upon exiting the gel region (not shown), the bands re-focus into one peak at the LE-TE interface, allowing for in-line (downstream) processes to be implemented.

Figure 4E:
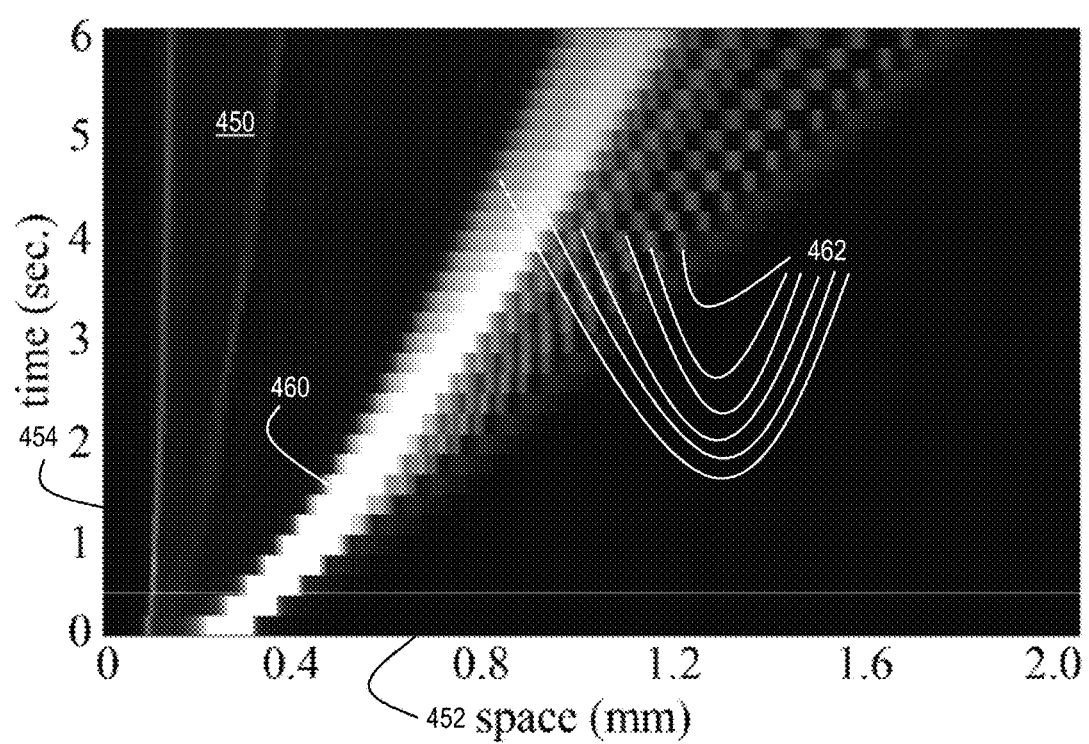
FIG. 4E is a graph that illustrates example measurements corresponding to the arrangements of FIG. 4C and FIG. 4D, according to an embodiment.

FIG. 4E is a graph 450 that illustrates example measurements corresponding to the arrangements of FIG. 4C and FIG. 4D, according to an embodiment. The horizontal axis is distance along the channel 110 in millimeter (mm, 1 mm=10$^{-3}$ meters); and, the vertical axis is time in seconds. At each time (e.g., about every 0.2 seconds) an image of the fluorescence in a 2 mm portion of the channel is collected. The polymer gel occupies a portion of the channel from about 0.9 mm to about 1.3 mm. The single bright fluorescent peak 460 observed in the first 0.5 mm and first second of the ITP clearly gives way to multiple fainter peaks 462 in the region of the gel at times after about 2 seconds.

4.2 Quantification of microRNA

MicroRNAs (miRNAs) are a growing class of small, noncoding RNAs (17-27 nucleotides) that regulate gene expression by targeting mRNAs for translational repression, degradation, or both. These molecules are emerging as important modulators in cellular pathways such as growth and proliferation, apoptosis, and developmental timing. To date, thousands of miRNAs have been identified in organisms from viruses to primates through cloning and sequencing, or computational prediction based on strong conservation of miRNA sequence motifs.

The most popular and well-established miRNA profiling methods are adapted from traditional nucleic acid analysis techniques. These include northern blot, microarrays, sequencing and reverse-transcription PCR (RT-PCR). Microarrays and sequencing platforms have high throughput but require significant instrumentation, amount of sample (about 5 µg of total RNA), are time consuming and require pre-amplification which yields significant sequence bias. RT-PCR has high dynamic range and is sensitive but has low throughput and is less specific than standard PCR. Lastly, northern blot has moderate sensitivity and allows for length discrimination of sequences, but remains time consuming and requires large amounts of sample (often>1 µg of total RNA). Northern blotting consists of gel electrophoresis for separation of total RNA with subsequent transfer to a nitrocellulose membrane, followed by hybridization with a radioactively labeled probe visualized with a scintillation counter.

The technique of spatial gradient additives has been used for the sensitive and selective absolute quantification and isolation of miRNA in an RNA sample, as described in greater detail below. In this example, a three-zone ITP channel with varying concentrations of largely non-ionic polymer sieving matrix and denaturant and label. These three serial zones allowed for consecutive pre-concentration, selection and quantification of miRNA.

Figure 5A:
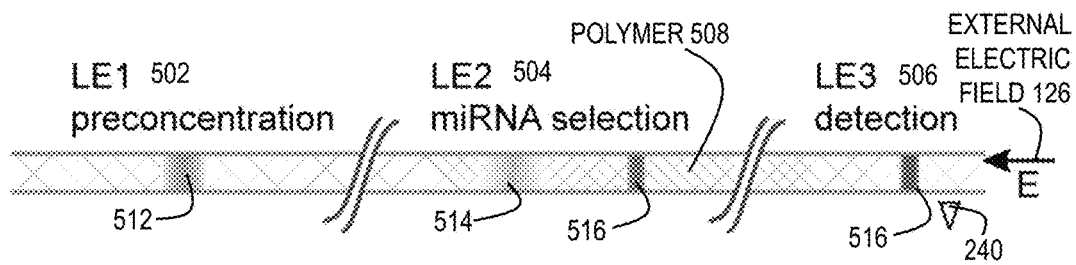
FIG. 5A through FIG. 5D are block diagrams that illustrates example pre-concentration of the analyte in a first zone, separation of similar speed ions by size using a higher concentration of one additive in a second zone, and detection using a lower concentration of another additive in a third zone, according to an embodiment.

FIG. 5A through FIG. 5D are block diagrams that illustrates example pre-concentration of the analyte in a first zone, separation of similar speed ions by size using a higher concentration of one additive in a second zone, and detection using a lower concentration of another additive in a third zone, according to an embodiment. FIG. 5A shows a pre-concentration first zone 502, an miRNA selection second zone 504 and a detection third zone 506, as well as the direction of external electric field 126. Concentration of polymer 508 in solution is indicated by cross hatching in which wider separation indicates lower concentration of the polymer in solution. The polymer concentration increases to a maximum in the second zone 504. In the preconcentration zone 502 the first LE mixture (e.g., LE1 described above with reference to FIG. 2A) allows both miRNA and RNA ions to focus at the interface 512 between TE and LE ions. In the miRNA selection zone 504 the second LE mixture (e.g., LE2 described above with reference to FIG. 2A) allows miRNA in a leading focused interface 516 and causes RNA ions to de-focus in a following population peak 514, with denaturing agents enhancing the separation. In the detection zone 506 the third LE mixture (e.g., LE3 described above with reference to FIG. 2A) labels the miRNA in the leading focused interface 516 without hindrance by denaturing agents.

For example, in this embodiment to quantify miRNA, one additive is a polymer in solution. The additive is used as a sieving matrix that serves to sieve more effectively as the concentration of the polymer increases. As the small target analyte (e.g., miRNA) moves from a region of low sieving matrix concentration to one of high sieving matrix concentration, it stays focused. However, molecules (such as RNA) of longer-than-targeted length have a mobility which drops below that of the TE in the presence of high concentrations of the sieving matrix, and so get left behind and are no longer focused in the zones after passing such a high concentration zone.

The sieving matrix concentration is not uniform throughout the channel because it is desirable to have low sieving matrix concentration in the first zone to allow a less specific, preliminary sorting of RNA from longer RNA while still maintaining a relatively high value of RNA mobility. The latter maintains a high rate of accumulation of RNA into the ITP focus zone (the interface between TE and LE). This allows for higher accumulation rate in a shorter channel length. However, once this preliminary sorting and high rate accumulation are accomplished, the sample propagates into a second zone. The second zone uses higher sieving matrix concentration to achieve separation of miRNA from slightly longer RNA which has slightly lower mobility in local sieving matrix concentration.

To allow the sieving matrix to more effectively interact with and slow down the longer RNA chains, a denaturing agent is also included in the first and second zones. The denaturing agent mitigates tight folding of the RNA chains so that more interaction occurs with the sieving matrix and sieving can be more effective. By the third zone, the longer RNA chains are no longer traveling in the focused sample at the interface; and, denaturing conditions are much less important. Furthermore, a label is included as an additive in the third zone, and high concentration of this denaturing agent interferes with the binding of this label to the miRNA. Thus label concentrations are increased in the third zone and denaturing concentrations are decreased. The concentration of denaturant is decreased in the third zone because the fine separation of short RNA from slightly longer RNA is not required in the third zone (since the slightly longer RNA have been left behind a significant distance). This helps improve the focusing dynamics of the focused RNA to improve sensitivity of the assay.

Therefore, in this example embodiment, the sieving additive is low in the first zone, and high in the second zone, and again lower in the third zone. The denaturing agent additive concentration is high in the first two zones and low in the third zone. And the label additive concentration is zero in the first zone and significant in the second and third zones.

Figure 5B:
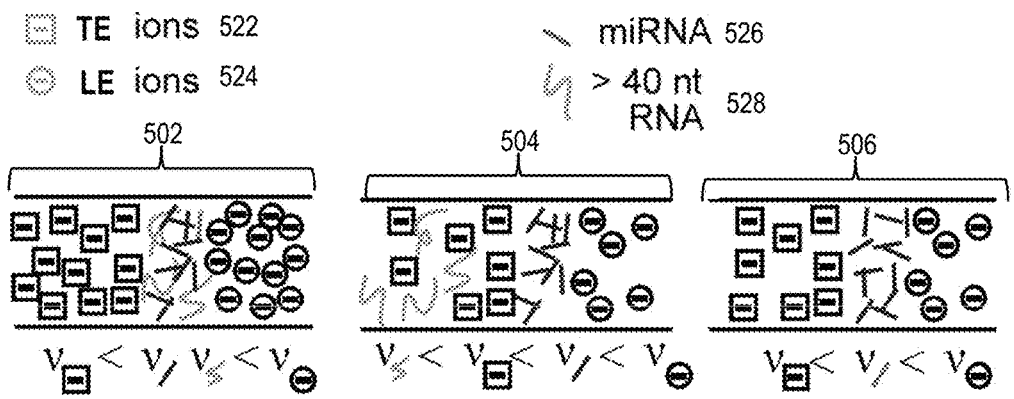

FIG. 5B is a block diagram that depicts TE ions 522, LE ions 524, miRNA ions 526 and large RNA ions (with greater than 40 nt) 528, each with corresponding mobility magnitudes represented by the symbol "V," in each of the three zones 502, 504 and 506. In zone 502 both miRNA 526 and RNA 528 have mobilities between the mobility of TE ions 522 and the mobility of LE ions 524. In zone 504, the mobility of RNA falls below that of the TE ions 522 and those molecules fall out of focus at the interface. In zone 506 the remaining miRNA ions 526 take up a fluorescent label (not shown) and stay focused between the TE ions 522 and the LE ions 524.

Thus, in some embodiments, a first additive comprises a polymer that provides a sieving matrix. Further, in some embodiments, the analyte is a nucleotide and a second additive comprises a denaturing agent. Furthermore, in some embodiments, a third additive comprises a fluorescent label.

This is accomplished in an experimental embodiment with the following experimental procedures. During step 305 the channel is prepared in the off-the-shelf chip design (model NS260, Caliper LS, Mountain View, Calif.) as shown on FIG. 2A. Before each set of experiments, the chip is first preconditioned by rinsing the channels successively with 100 milliMoles (mM, 1 mM=$10^{-3}$ Moles) sodium hydroxide for 5 minutes (min), deionized (DI) water for 1 min, 100 mM hydrochloric acid for 5 min, and DI water for 1 min. The different LE mixtures are then added to reservoirs 212, 220 and 214 as follows, 5 microliters (ml, 1 ml=$10^{-6}$ liters) of LE1 into each of ports 212, 222, 223; of LE2 into each of ports 224, 225, 226; and of LE3 into each of ports 227 and 214. A vacuum is applied to reservoirs 223 and 227 for 5 min. These initial rinsing and filling steps are useful to reduce and stabilize electroosmotic flow in the borosilicate chip.

The LE mixtures all contain Tris hydrochloride (pH=8.0), urea, Polyvinylpyrrolidone (PVP). For RNA quantitation, we used SYTO RNAselect dye, except for the spatial temporal diagrams of FIG. 5C and FIG. 5D, described below, where we used SYBR Green II. The TE is a solution of 92.5% v/v formamide containing Tris and Caproic acid. We use urea in the LE1 and LE2 zones to increase separation resolution for greater accuracy, but this significantly decreases fluorescence of the RNA stain. Consequently, we use reduced denaturing conditions (low $C_d$) in LE3, so this last section acts as a detection zone.

Before each experiment, all reservoirs are rinsed with DI water. The different LE mixtures are added to reservoirs 212, 220 and 214 as described above and again a vacuum is applied to reservoir ports 223 and 227 for 2 min. Applying vacuum at port 223 creates an interface between LE1 and LE2 at the intersection A and applying vacuum at port 227 creates an interface between LE2 and LE3 at the intersection B. The vacuum is then released, the input port 214 is rinsed and emptied, and contacted with the mixture of TE and sample. Finally, a 3 kV potential difference is applied between output port 214 and input port 212 to start the ITP process and a stop voltage is applied after the ITP interface has reached the detector using the high voltage power supply 232.

In an experimental demonstration of this process, a 22 nt analyte and 60 nt long RNA contaminant in a sample were focused in zone LE1 and the 60 nt long RNA contaminant was selectively defocused in zone 2. The sequences of the nucleic acids used in these experiments are given in Table 1.

TABLE 1

Sample nucleic acids in various experiments.

| Length (name) | SEQ. ID NO. | Sequence (5' to 3') |
|---|---|---|
| 23 nt (miR-17) | 1 | CAAAGUGCUUACAGUGCAGGUAG |
| 40 nt | 2 | CUGUGACACUUCAAACUCGUACCG UGAGUAAUAAUGCGCC |
| 60 nt | 3 | CAUUAUUACUUUUGGUACGCGCUGU GACACUUCAAACUCGUACCGUGAGU AAUAAUGCGC |
| 22 nt (miR-126) | 4 | UCGUACCGUGAGUAAUAAUGCG |
| 22 nt (complimentary to miR-126) | 5 | CGCAUUAUUACUCACGGUACGA |

Figure 5C:
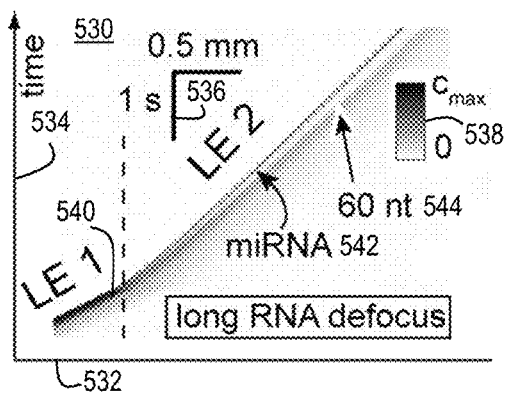
Figure 5D:
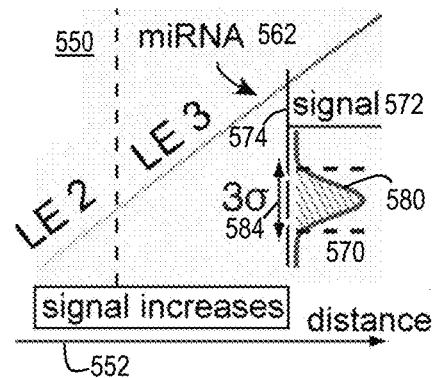

FIG. 5C is a spatiotemporal plot 530 of the population peaks of the two RNA species in the transition from zone LE1 to LE2; and FIG. 5D is a spatiotemporal plot 550 of the population peak of the smaller 22 nt RNA species in the transition from zone LE2 to LE32. Plot 530 has horizontal axis 532 representing distance along channel and a vertical axis 534 representing time. Plot 550 has horizontal axis 552 representing distance farther along the channel and a vertical axis (not shown) representing a later time. Both plots share distance and time scale bars 536 representing 1 second vertically and 0.5 mm horizontally. Illumination is indicated by grayscale given by scale bar 538. The fluorescent signal at the detection point is represented by trace 580 on insert graph with horizontal axis 572 representing signal strength and vertical axis 584 representing cross channel distance. The amount of analyte is represented by the area under a gaussian fit to the signal that is three standard deviations ($3\sigma$) wide centered on the peak.

FIG. 5C shows channel-width-averaged fluorescence intensity (inverted grey scale) versus axial channel distance and time. Here, a mixture of 22 nt and 60 nt long RNA focus in LE1, but only the 22 nt RNA remains focused in LE2. FIG. 5D shows transition of a 22 nt RNA focused peak from low fluorescence in LE2 to significantly larger fluorescence in LE3. Recall that the LE3 zone has reduced denaturant concentration enabling higher fluorescence for sensitive quantification of the selectively focused miRNA.

To perform exquisitely selective miRNA focusing, we first chose a TE whose mobility was smaller than the mobility of short nucleic acids (for zero $C_p$), and chose nominal values for $C_p$ in LE1 and 2. We then performed a series of experiments with increasing $C_p$ (and decreasing local RNA mobility) in LE2. Such titration allowed tuning of the cut-off focusing length (length below which RNA focuses).

Figure 6A:
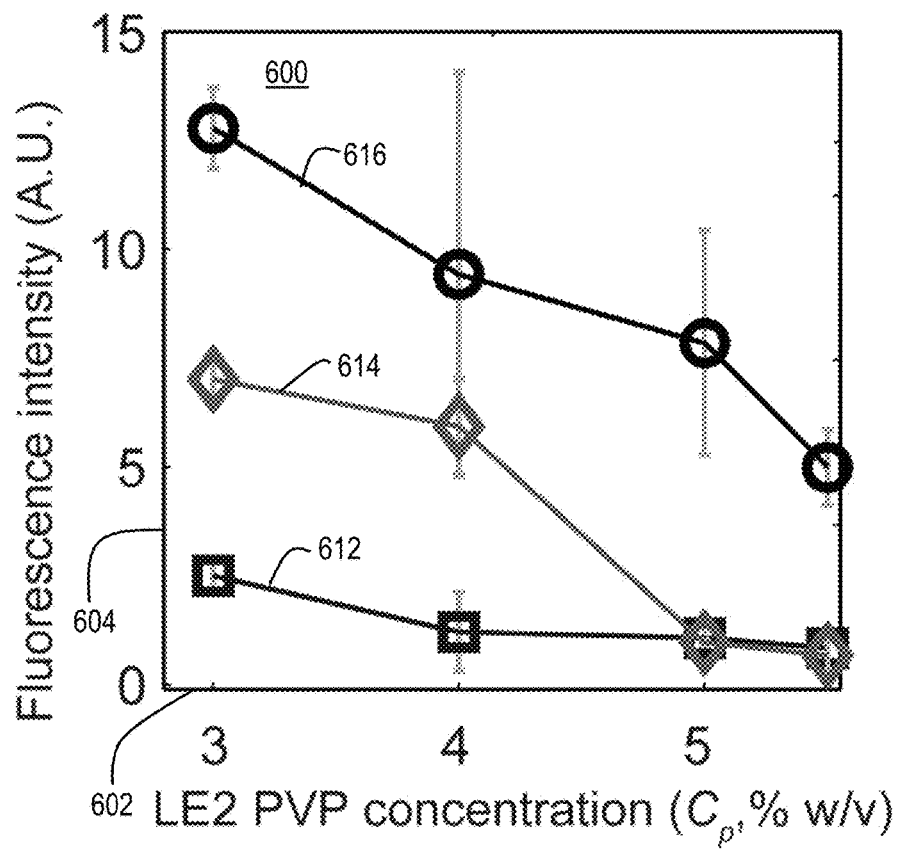
FIG. 6A through FIG. 6B are graphs that illustrate example dependence of selectivity on polymer concentration as additive, according to an embodiment.
Figure 6B:
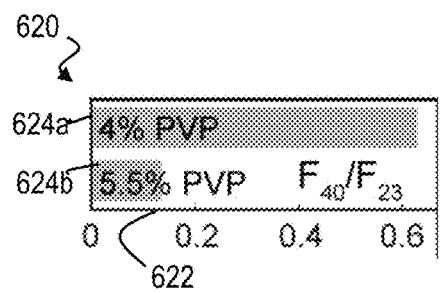

In FIG. 6A, results are shown of three sets of titration experiments using 23 and 40 nt synthetic oligoribonucleotides and yeast tRNA. A 40 nt long synthetic oligo was used to simulate RNA longer than miRNA, and tRNA (80 nt in average) to verify that highly abundant short RNAs with strong secondary structures do not interfere with the measurement. The titration aimed at finding the $C_p$ to focus miRNA but reject 40 mer and tRNA. FIG. 6A and FIG. 6B are graphs 600 and 620, respectively, that illustrate example dependence of selectivity on polymer concentration as additive, according to an embodiment. In FIG. 6A, the horizontal axis 602 is concentration of polymer PVP in solution in the LE2 mixture; and, the vertical axis 604 is fluorescence intensity in arbitrary units. In these experiments 23 nt and 40 nt long RNA and tRNA as a sample with analyte and contaminant, respectively, were dissolved in the TE. Total intensity in the focused zone is reported for increasing polymer concentration in LE2. All RNA focus at 3% weight/volume (w/v) PVP. At 5% w/v and above, significant focusing of the 23 nt RNA is still observed while both 40 nt and tRNA are rejected.

In FIG. 6B, the horizontal axis 622 is ratio of concentration of the 40 nt oligo to the 23 nt oligo; and the vertical axis indicates two values for the polymer PVP concentration in solution. At 4% w/v PVP, $F_{40}/F_{23}$ is greater than 0.6, but drops down to 0.12 at 5.5% w/v. This led to the choice to use 5.5% w/v PVP in LE2 for selective focusing of miRNA.

For all three RNAs, the amount of focused RNA gradually decreased with increasing PVP initial concentration in LE2. This is consistent with a global decrease of nucleic acid electrophoretic mobility, and associated decreased flux of RNA to the ITP interface. At 3% w/v PVP, there was significant focusing of all three RNA types. Increasing PVP concentration to 4% w/v resulted in defocusing of tRNA, shown by the drop in tRNA signal to the baseline value. 40 nt RNA was rejected at 5% w/v PVP. Meanwhile, the amount of 23 nt long RNA remained significant at all concentrations. In particular, at 5.5% w/v PVP, the measured (baseline) fluorescence intensity of the 40 nt RNA case was only 12% of the fluorescence of miRNA, but exceeded 60% of miRNA at 4% w/v. We attribute most of the residual fluorescence at 5.5% w/v to contamination and synthesis byproducts remaining after purification of the 40 nt oligo. This titration shows refined selective focusing of miRNA with an LE2 with 5.5% w/v PVP and an RNA cutoff length between about 24 and 39 nt.

Figure 6C:
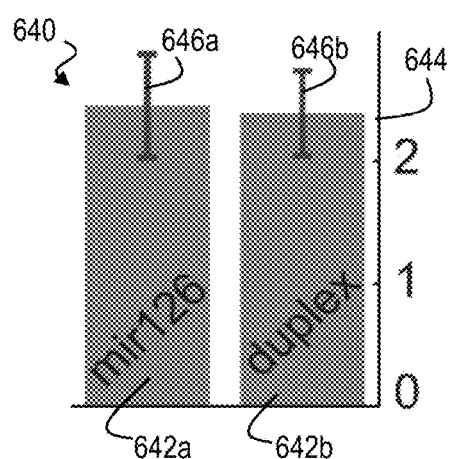
FIG. 6C is a graph that illustrates example effectiveness of denaturant as additive, according to an embodiment.

FIG. 6C is a graph that illustrates example effectiveness of denaturant as additive, according to an embodiment. The horizontal axis indicates niR-126 and hybridized with a complementary sequence (duples). The vertical axis is fluorescence intensity in arbitrary units. This shows results of selective focusing of miR-126 (5 pg·µl$^{-1}$ in TE) and of an equimolar mixture of mir-126 and its complementary RNA (each at 2.5 pg·µl$^{-1}$). There is no significant difference between fluorescence of miR-126 and of the duplex, showing no bias due to base pairing. Uncertainty bars 646a, 646b represent 95% confidence interval. The results show that secondary structure of tRNA had no discernable effect on assay selectivity, e.g., that the amount of denaturant is sufficient to prevent secondary structure.

Figure 7:
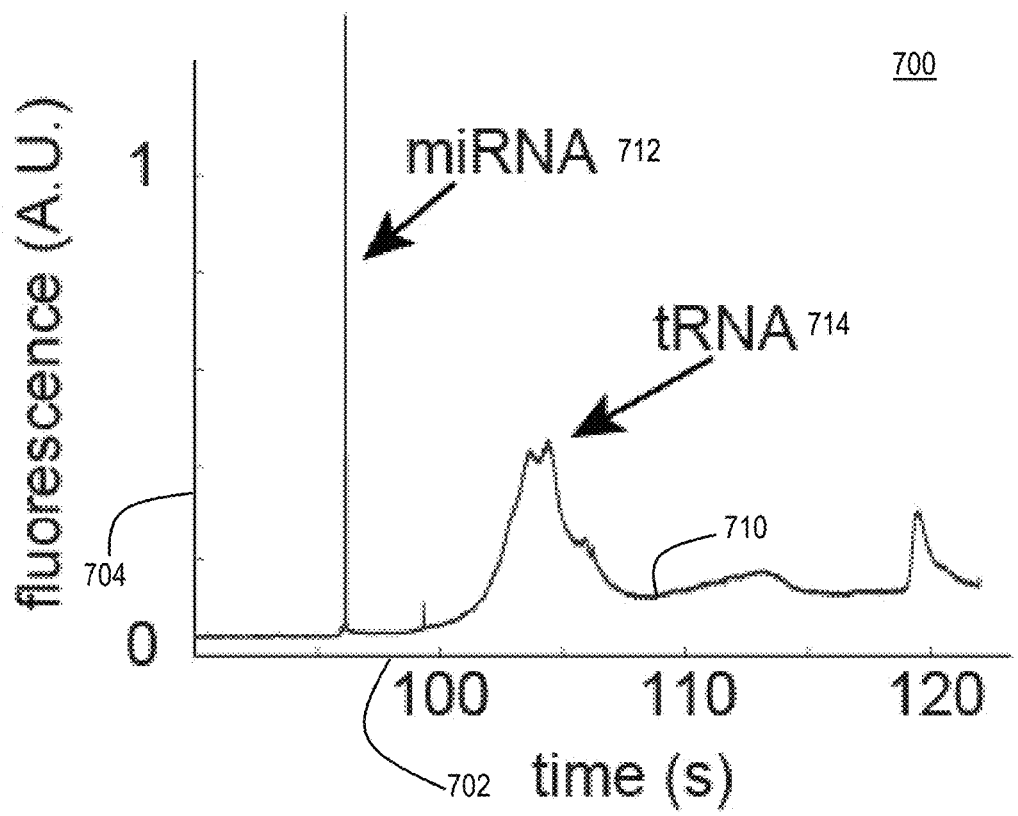
FIG. 7 is a graph that illustrates typical example isotachopherogram of selective focusing of miRNA from total RNA, according to an embodiment.

FIG. 7 is a graph 700 that illustrates typical example isotachopherogram of selective focusing of miRNA from total RNA, according to an embodiment. The horizontal axis 702 is time in seconds a the viewing port near the output (exit) port. The vertical axis 704 is fluorescence in arbitrary units. The trace 710 is a measurement at the viewing point. The first arrival is the focused miRNA at peak 712. A much later arrival is a much less focused peak of longer RNA molecules, such as tRNA peak 714. The sharp peak 712 at t=92 s corresponds to the ITP focused miRNA. This peak is approximately Gaussian with characteristic width around 20 ms. The peak(s) 714 at larger migration times (t>100 s) corresponds to longer RNA molecules, most likely transfer RNA (tRNA). For each run, a Gaussian fit on the miRNA peak was performed and the signal was integrated over three standard deviations, centered on the peak position. This run corresponds to a typical miRNA quantitation run for Hepa1-6 cells (5 ng·µl−1 in the TE). Before continuing, we note we performed similar measurements on degraded RNA samples, and these showed significant tailing of the miRNA peak, a dispersed tRNA peak, and overlap between these. Degraded RNA samples also showed abnormally high levels of focused short RNA compared to higher quality preparations. Under such conditions, degraded RNA likely produced fragments shorter than the ITP cutoff length, resulting in highly upward biased quantitation of miRNA. To avoid this bias, we systematically obtained RNA integrity numbers (RIN, measured at the Stanford PAN facility) for all samples and performed measurements exclusively on samples with RIN greater than 9.0, which exceeds recommendations for miRNA analysis.

Figure 8A:
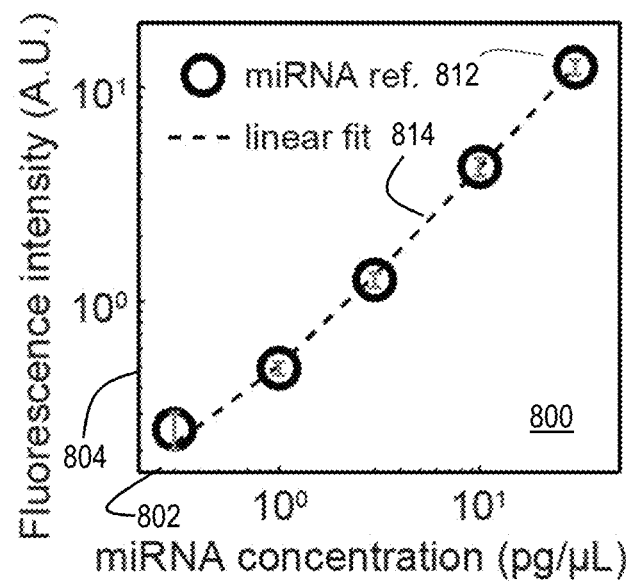
FIG. 8A is a graph that illustrates an example calibration curve for absolute quantification of miRNA using selective ITP, according to an embodiment.

Calibration curves were determined by diluting the miRNA reference in the TE at relevant concentrations. FIG. 8A is a graph that illustrates an example calibration curve for absolute quantification of miRNA using selective ITP, according to an embodiment. The horizontal axis 802 is miRNA concentration in picograms per microliter (pg/µL, 1 pg=10$^{-12}$ grams and 1 mL=10$^{-6}$ liters). Points 812 are measurements and trace 814 is a linear fit. The miRNA concentration varied between 0.3 and 30 pg·µL$^{-1}$. Negative controls (experiments with no miRNA in the TE) yielded a reproducible fluorescent signal at the 0.1 pg·μL$^{-1}$ level. This residual fluorescence was likely due to contamination of stock chemicals as observed routinely by us and others using ITP.

Figure 8B:
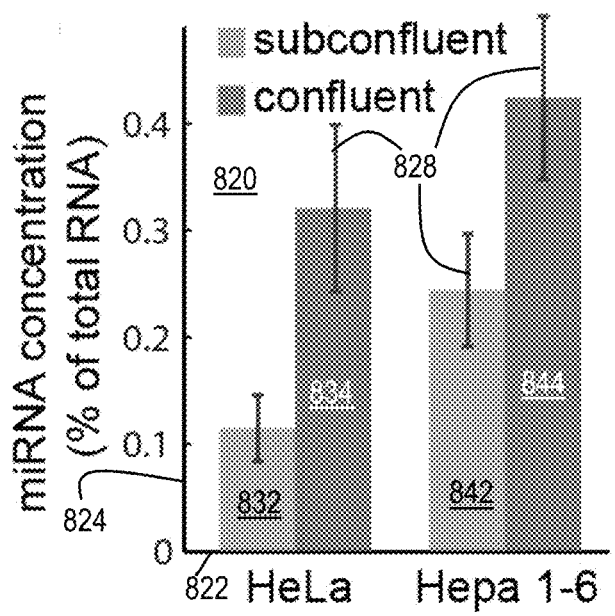
FIG. 8B is a graph that illustrates an example quantitative assessment of miRNA in Hepa1-6 and HeLa cell cultures before (low density) and at confluence (high density), according to an embodiment.

To demonstrate the efficacy and utility of this ITP assay in a strongly relevant biological application, we quantified global miRNA levels in subconfluent and confluent cell cultures. Hwang, H. W.; Wentzel, E. A.; Mendell, J. T. Proceedings of the National Academy of Sciences of the United States of America 2009, 106, 7016-7021 (hereinafter, Hwang et al.) showed that cell-cell contact activates miRNA biogenesis, resulting in greater miRNA abundance in densely-grown cultures of various cell lines. Herein is provided further independent evidence for this effect using the ITP-based selective quantitation by measuring miRNA abundance in HeLa and Hepa1-6 cell cultures before and at confluence. FIG. 8B is a graph that illustrates an example quantitative assessment of miRNA in Hepa1-6 and HeLa cell cultures before (low density) and at confluence (high density), according to an embodiment. The horizontal axis 822 indicates a grouping of data; the vertical axis 824 indicates miRNA concentration as a percent of total RNA in sample as measured using selective ITP with gradients in one or more additives. Bar 832 and bar 842 represent HeLa and Hepa1-6, respectively, at low density. Bar 834 and bar 844 represent HeLa and Hepa1-6, respectively, at high density. The error bars 828 represent 95% errors.

For these graphs, miRNA quantitation was performed with ITP as described above. Absolute miRNA abundance from total RNA was measured from subconfluent and confluent cultures. The results for HeLa and Hepa1-6 cells in FIG. 8B are presented as percentage of total RNA (since total RNA concentration does not vary with cell density). In both cases, a significant increase was observed in miRNA expression between the subconfluent and confluent cultures. miRNA levels increased from 0.11% to 0.32% of total RNA in HeLa cells, and from 0.24% to 0.42% in Hepa1-6 cells. These results provide independent validation of the findings reported in Hwang et al. and confirm the efficacy of the ITP based miRNA quantification. While relative values of miRNA levels were qualitatively similar to Hwang's study, it is noted that the current measurements show slightly larger concentrations of miRNA than levels estimated from microarray data. We attribute this apparent discrepancy to variations of miRNA expression between different cell types and to different small RNA extraction efficiencies associated with the preparation method.

4.3 Molecular Beacons for microRNA

Figure 9A:
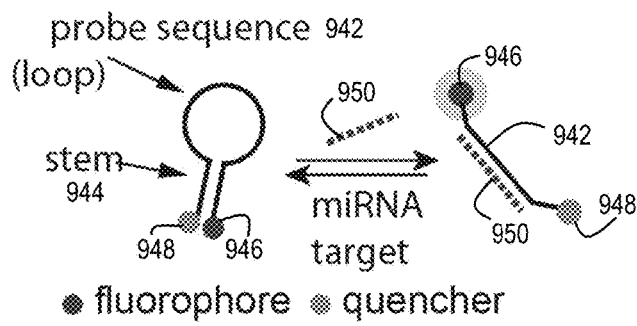
FIG. 9A is a block diagram that illustrates a sequence specific molecular beacon, used in some embodiments.

Molecular beacons are sequence specific nucleic acid probes that fluoresce upon hybridization. Developed in the early years of quantitative PCR, molecular beacons have become ideal sequence-specific fluorescent reporters for nucleic acid amplifications assays and in vivo hybridization. The sequence specific fluorescence of MBs originates from their unique structure shown in FIG. 9A. FIG. 9A is a block diagram that illustrates a sequence specific molecular beacon (MB), used in some embodiments. MBs are composed of four units: (i) a nucleic acid probe sequence 942 (in a loop up to about 30 nt long) complementary to the target sequence of interest, e.g., on the analyte; this sequence is flanked by (ii) two, complementary self-hybridizing sequences in the stem 944 which allow conformation of the probe into a hairpin structure, (iii) a fluorophore 946 at the 5' end, and (iv) a suitable quencher 948 at the 3' end. When the molecular beacon is free in solution, it acquires a hairpin structure which brings 5' and 3' ends to proximity, so the quencher hampers fluorescence. In the presence of a sequence 950 complementary to the probe, the hairpin opens and hybridizes to the target sequence 950, e.g., as found in an analyte. This is thermodynamically favorable because the short stem hybrid 944 is less stable than the longer probe-target hybrid. In this configuration, the distance between fluorophore and quencher is sufficient to enable fluorescence.

Here is presented a different hybridization strategy than conventionally used for miRNA detection and quantification, which leverages isotachophoresis (ITP) and hybridization with molecular beacons (MBs) for the profiling of miRNA. In contrast to conventional methods, this assay is a single, amplification-free process which simultaneously purifies, preconcentrates, actively mixes, hybridizes, and produces an optical signal whose intensity increases with the initial target sample concentration. The technique of spatial gradient additives is used. Here, a three-stage ITP channel with varying concentrations of (electrically neutral) polymer sieving matrix and denaturant is also used. However, in the third zone, a labeled probe is used to label only certain sequences of miRNA through hybridization of the probe with the target miRNA. In some embodiments, the third zone includes one or more additives to encourage hybridization or label sensitivity. In the illustrated embodiment, magnesium ion in the channel is also introduced as an additive to promote hybridization. These three serial zones allowed for consecutive pre-concentration, selection and hybridization of miRNA. Thus, in some embodiments, the analyte is a nucleotide and a fourth additive comprises a nucleotide probe with a fluorescent label.

Figure 9B:
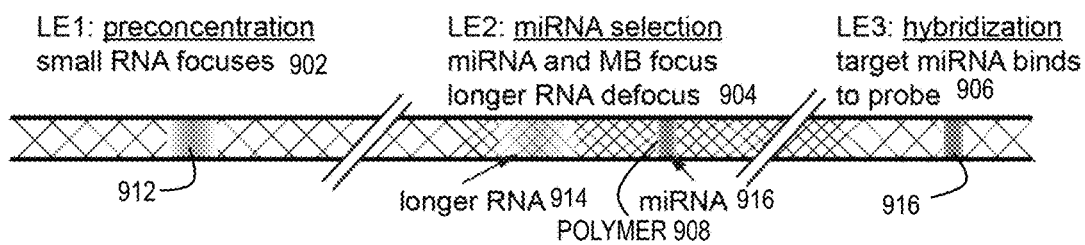
FIG. 9B and FIG. 9C are block diagrams that illustrate pre-concentration of the analyte in a first zone, separation of similar speed ions by size using a higher concentration of one additive in a second zone, and detection using hybridization with molecular beacons based on higher concentration of another additive in a third zone, according to an embodiment.

FIG. 9B and FIG. 9B are block diagrams that illustrate pre-concentration of the analyte in a first zone, separation of similar speed ions by size using a higher concentration of one additive in a second zone, and detection using hybridization with molecular beacons based on higher concentration of another additive in a third zone, according to an embodiment. FIG. 9B depicts a preconcentration first zone 902, an miRNA and MB selection second zone 904 and a hybridization and detection third zone 906. Concentration of polymer 908 in solution is indicated by cross hatching in which wider separation indicates lower concentration of the polymer in solution. The polymer concentration increases to a maximum in the second zone 904. In the preconcentration zone 902 the first LE mixture (e.g., LE1 described above with reference to FIG. 2A) allows miRNA and RNA ions to focus at the interface 512 between TE and LE ions. In the miRNA selection zone 904 the second LE mixture (e.g., LE2 described above with reference to FIG. 2A) allows miRNA in a leading focused interface 916 and causes RNA ions to de-focus in a following population peak 914, with denaturing agents enhancing the separation. In the hybridization and detection zone 906 the third LE mixture (e.g., LE3 described above with reference to FIG. 2A) labels the miRNA in the leading focused interface 516 without hindrance by denaturing agents.

Figure 9C:
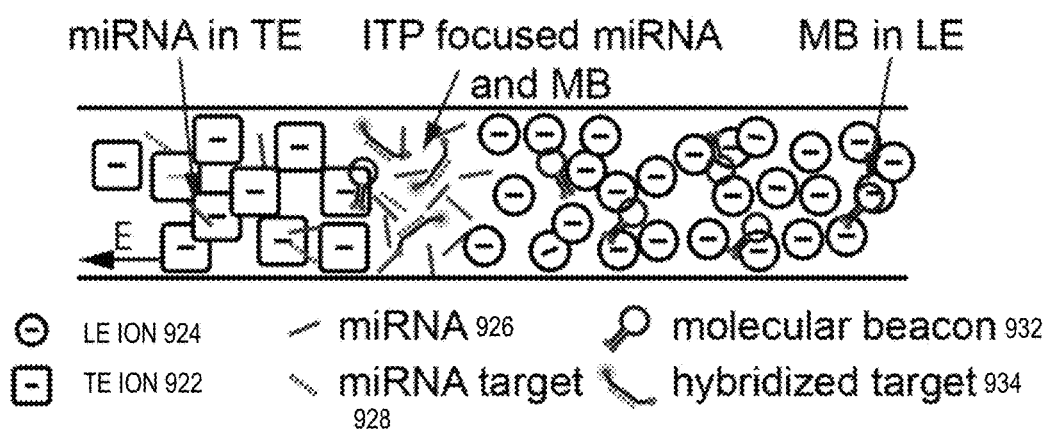

FIG. 9C is a block diagram that depicts TE ions 922, LE ions 924, miRNA ions 926, miRNA target ions 928 that have the target sequence, molecular beacon molecules 932 in the LE3 mixture that will bind only to the miRNA target ions, and hybridized target molecules 934 in the ITP focused interface of the third zone 906. In zone 906 the miRNA target ions 926 take up a molecular beacon 932 and stay focused between the TE ions 922 and the LE ions 924

Here, mature miRNA (18 to 24 nt) are selectively focused and all RNA molecules longer than 60 nt rejected from the ITP zone. Therefore bias is avoided from hybridization of long RNAs that contain identical or similar sequences. In particular, the 70 nt long miRNA precursors pre-miRNA are excluded. This selectivity combined with the simultaneous hybridization is in some ways similar to the process of northern blotting, which requires multiple successive steps including electrophoresis and hybridization to achieve detection. In contrast to northern blotting, ITP here provides simultaneous preconcentration and active mixing of target and probe prior to and during detection.

The sample is mixed in the TE which includes 5 mM MOPS, 5 mM Tris and 92.5% v/v formamide. TE and sample are loaded into the input port 212 of FIG. 2A. In the first zone mixture LE1, a low (0.5% w/v PVP) sieving matrix polymer concentration and 7 M urea are included. The mobility of miRNA increases with decreasing polymer concentration, so LE1 yields a strong flux of RNA to the ITP interface, but molecules longer than (mature) miRNA molecules are also focused. Also, the slightly larger concentration of leading ions in LE1 (50 mM) augments ITP preconcentration dynamics. The second zone with mixture LE2 has large polymer concentration (3% w/v PVP), which globally decreases mobility of RNA. This defocuses longer RNA (they fall behind and out of the ITP focus zone) while leaving miRNA and MB focused, at the cost of locally retarding focusing dynamics. As discussed below, the cut off length is below 60 nt, so that miRNAs can focus, but pre-miRNAs cannot focus. Finally, mixture LE3 in the third zone has low denaturing conditions (2 M urea, lower polymer concentration of 0.5% w/v), and optimized magnesium chloride concentration (2 mM $Mg^{2+}$). These conditions enable fast hybridization, and optimize fluorescence signals as miRNA targets specifically bind to MBs.

Initially, MB probes targeting the miRNA of interest are dissolved in the three LE mixtures, and total RNA (which includes miRNA) is dissolved in the TE. Leading and trailing ions are selected so that their mobilities allow for simultaneous and co-located focusing of miRNA including target miRNA, MB probe, and the miRNA-probe hybrid. (The latter ITP format which focuses multiple analytes into a common, sharp zone is called peak mode ITP.) Under this condition, miRNA and MB and the hybrid simultaneously focus at the interface between TE and LE. In the laboratory frame, miRNA overspeed TE ions and other RNA, and migrate toward the ITP zone. At the same time, the ITP zone overtakes and focuses MBs initially in the LE, so target and probe are actively preconcentrated and driven into themigrating ITP interface. In this focused interface, and under optimized conditions, miRNA hybridizes to the probe sequence of the MB, disrupting their hairpin structure and yielding a sequence-specific increase in fluorescence intensity within this ITP interface. This way, the focused interface acts as a reactor volume defined by its axial width and the cross sectional area of the microchannel. In the 44 micron wide, 12 micron deep channel of chip 200, the volume of the ITP reaction zone is on the order of 10 pL, given observed ~10 micron wide ITP interfaces. This is a significantly smaller reaction volume compared to existing microfluidic reactors, which are at least on the order of few nanoliters. The strong preconcentration dynamics (on the order of $10^3$ to $10^4$ fold increase of reactants in these conditions) yield improved kinetics and sensitivity.

Leading electrolytes contain DNase- and RNase-free Tris hydrochloride buffer (pH=8.0) from Invitrogen of Carlsbad, Calif., polyvinylpyrrolidone (PVP, M.W.=1,000,000) from Polysciences Inc. of Warrington, Pa., urea from EMD biosciences of Gibbstown, N.J., and magnesium chloride from EMD biosciences. Concentrations in mixtures LE1, LE2 and LE3 are respectively 50, 20 and 20 mM of Tris hydrochloride; 0.5% w/v, 3% w/v and 0.5% w/v of PVP; 7, 7, and 2 M of urea; 0, 2 and 2 mM of magnesium chloride. The TE is a solution of 5 mM Tris from Sigma-Aldrich of Saint Louis, Mo., and 5 mM MOPS from Sigma-Aldrich in 92.5% v/v formamide UltraPure from Invitrogen. All solutions were prepared with DNase- and RNase-free deionized water from Gibco of Carlsbad, Calif.

HPLC-purified molecular beacons and synthetic miRNA were purchased from Integrated DNA Technologies of Coralville, Iowa DNA molecular beacons, 5'-labeled with TYE 665 fluorescent dye (excitation at 645 nm and emission at 665 nm) and 3'-labeled with Iowa Black RQ quencher (peak absorbance at 656 nm) were used. The precursor mir-26a was synthesized and PAGE-purified by Dharmacon of Lafayette, Colo. The sequences of synthetic oligoribonucleotides and probes used in this work are listed in Table 2. For molecular beacons, TYE 665 is a fluorophore (with spectrum similar to Cy5) and Iowa Black RQ (IBRQ) is the quencher. The miRNAs and precursor are ribonucleic acids while molecular beacons are deoxyribonucleic acids. For molecular beacons, the complementary stem-forming sequence fragments are underlined. Total RNA from normal human liver and kidney were obtained from as FirstChoice human total RNA from Ambion of Austin, Tex. Before each experiment, the sample (total or synthetic RNA) was dissolved to the specified concentration in 50 μL of TE, placed in a water bath at 70° C. for 5 min and finally on ice until running the ITP hybridization experiment. Separately, the MB was dissolved in 500 μL of each LE mixture.

TABLE 2

Nucleic acids used in molecular beacon experiments

| Oligo name (length) | SEQ. ID. NO | Sequence (5' to 3') |
| --- | --- | --- |
| miR-26a (22 nt) | 6 | UUCAAGUAAUCCAGGAUAGGCU |
| miR-126 (22 nt) | 4 | UCGUACCGUGAGUAAUAAUGCG |
| miR-122 (22 nt) | 7 | UGGAGUGUGACAAUGGUGUUUG |
| mir-26a (77 nt) (miR-26a precursor) | 8 | GUGGCCUCGUUCAAGUAAUCGGAUACA GGCUGUGCAGGUCCCAAUGGGCCUAUU CUUGGUUACUUGCACGGGACGC |
| miR-26a MB (34 nt) | 9 | TYE665-CCGAGCAGCCTATCCTGGAT TACTTGAAGCTCGG-IBRQ |
| miR-122 MB (34 nt) | 10 | TYE665-CCGAGCCAAACACCATTGTC ACACTCCAGCTCGG-IBRQ |

10A is a graph that illustrates example demonstration of the ITP hybridization assay compared to a control, according to an embodiment. The horizontal axis 1002 is time in seconds; and, the vertical axis 1004 is fluorescence intensity in arbitrary units. Trace 1010 represents a negative control displaced +0.5 s and +0.7 A.U. on the plot for clarity of presentation. Trace 1012 represents a sample with target miRNA. The traces represent two isotachopherograms acquired 8 mm into the LE3 zone. In both experiments, the LE contains 1 nM of MB targeting miR-26a. The upper trace 1010 corresponds to a negative control experiment where the TE contains no RNA. This trace exhibits a peak which is attributed to imperfect quenching of the focused MB. The trace 1012 shows the result of ITP-hybridization where we added 1 nM of miR-26a target to the TE. The ITP peak has significantly greater amplitude compared to the negative control. This demonstrates successful combination of ITP and MB based hybridization for the detection of miRNA.

Figure 10A:
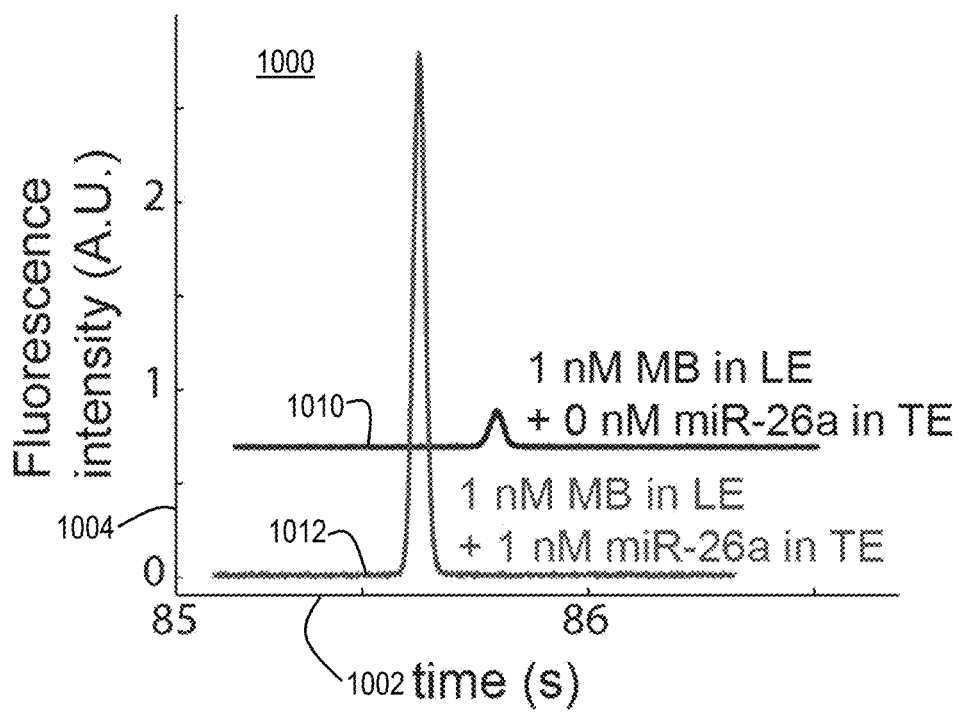
FIG. 10A is a graph that illustrates example demonstration of the ITP hybridization assay compared to a control, according to an embodiment.
Figure 10B:
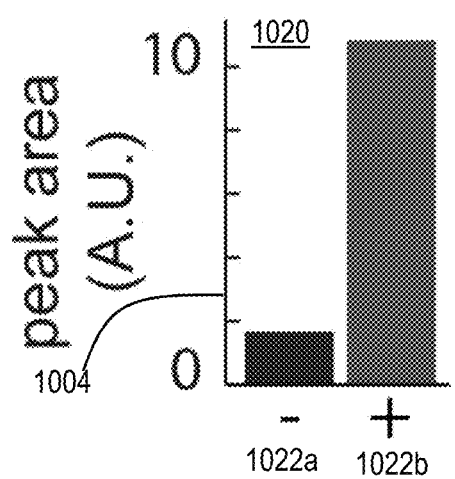
FIG. 10B is a graph that illustrates the area of each peak of the traces in FIG. 10A, according to an embodiment.

FIG. 10B is a graph 1020 that illustrates the area of each peak of the traces in FIG. 10A, according to an embodiment. Horizontal axis indicates negative control 1022 and sample with target miRNA 1022b. The vertical axis represents area in the peak in arbitrary units. The peak area of this experiment with 1 nM target in the TE (+) at 1022b is more than 6 times larger than the area of the negative control (−) at 1022a. This shows successful hybridization of the target and MBs within the focused zone.

For an ITP hybridization experiment with a peak area A, we define the relative fluorescence enhancement f as:

$$f = A/A_{nc} - 1,$$

where $A_{nc}$ is the peak area of the negative control, i.e. an experiment with equal MB concentration but a blank TE. In the embodiment presented in FIG. 10B, f is approximately 5.5. f theoretically varies between zero (when $A = A_{nc}$) and a saturation value where all focused MB are open. The latter occurs when the number of target copies in the focused zone is much larger than the number of MBs. We note that f is also a function of other parameters including MB concentration, MB stem sequence, miRNA melting temperature, and ITP chemistry.

Figure 11:
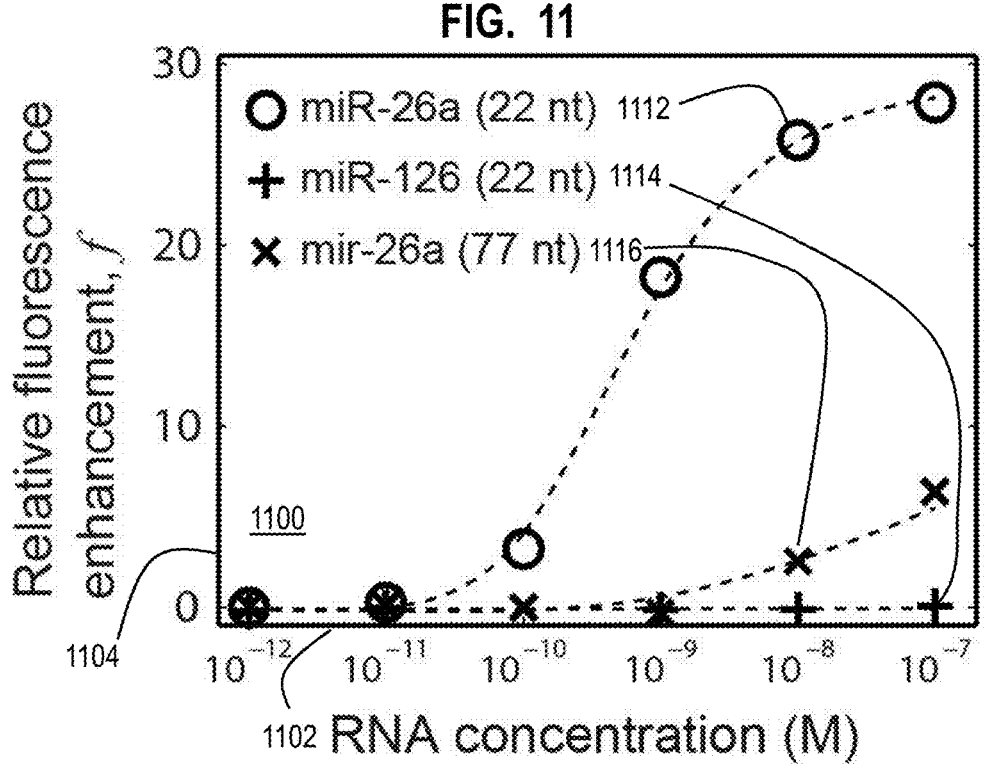
FIG. 11 is a graph that illustrates typical example fluorescence enhancements f for ITP hybridization, according to an embodiment.

The fluorescence enhancement of MBs increases with target concentration. In peak mode ITP, the amount of focused sample is a linear function of sample concentration in the TE. Consequently, in the ITP hybridization assay, f increases with target concentration in the TE. Titration experiments were performed to illustrate the effect of sample concentration on fluorescence enhancement. FIG. 11 is a graph that illustrates typical example fluorescence enhancements f for ITP hybridization, according to an embodiment. The horizontal axis 1102 is RNA concentration in moles (M); and, the vertical axis is relative fluorescence enhancement f.

FIG. 11 reports fluorescence enhancements f for ITP hybridization at 100 pM MB with miR-26a concentrations 1112 ranging from 1 pM to 100 nM in the TE (circles). To aid in data visualization, the data was fitted with spline functions (dashed lines). Titration with miR-26a shows the signal generated from hybridization of the perfectly matching target. Fluorescence enhancement remains small at low concentration (below 10 pM) and significantly increases at 100 pM and above. f plateaus over about 10 nM, where nearly all focused MBs are open. Potential unspecific hybridization was also verified by titrating with miR-126 (whose sequence is distinct from miR-26a) plotted as trace 1114, and observed that fluorescence enhancement remained approximately null at all concentrations. This confirms the specificity of MB hybridization in the ITP zone. Titration with the precursor large miR-26a sample indicated by trace 1116 shows only slow increase of fluorescence with concentration above 10 nM, since the longer molecules are filtered out by the ITP process in the polymer zone. This shows that ITP in the LE2 zone excludes miRNA precursors from the focused zone, and allows for selective hybridization on miRNA. That is, this demonstrate that in ITP hybridization, MBs bind specifically to the correct target sequence.

Figure 12:
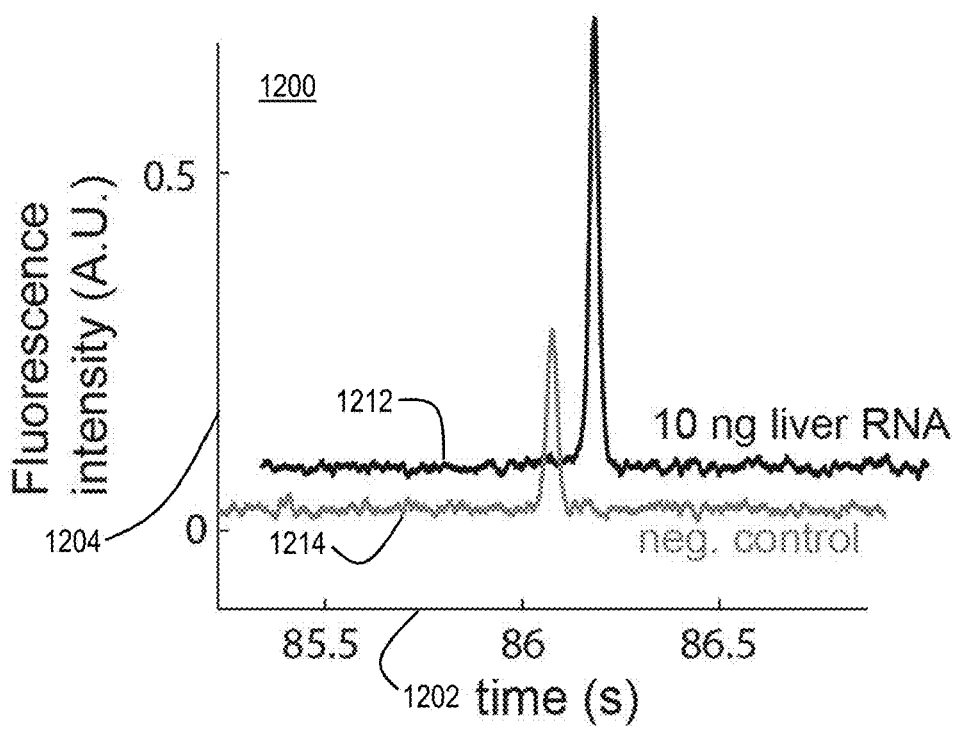
FIG. 12 is a graph that illustrates example results of the ITP hybridization assay for miRNA in liver tissue compared to a control, according to an embodiment.

To show the efficacy of the ITP hybridization assay in a biologically relevant case, detection of miR-122 was performed in two human tissue total RNA samples. The following liver-specific miRNA target was chosen for its large dynamic range of expression: miR-122 is highly expressed in liver but poorly expressed in other organs. We diluted total RNA from human liver and kidney in TE down to 10 ng·μL$^{-1}$. We then performed the ITP hybridization assay on these samples with 100 pM MBs in the LE targeting miR-122. FIG. 12 is a graph that illustrates example results of the ITP hybridization assay for miRNA in liver tissue compared to a control, according to an embodiment. The horizontal axis 1202 is time in seconds and the vertical axis 1204 is fluorescence intensity in arbitrary units. Trace 1212 indicates the results for the sample with liver cells and trace 1214 shows the results for a negative control. In both experiments, the LE contains 100 pM of MB targeting miR-122. Trace 1214 corresponds to a negative control where the TE contains no RNA. Trace 1212, displaced up and to the right for clarity of presentation, shows the result of ITP-hybridization where we added 10 ng·μL−1 of human liver total RNA to the TE. The ITP peak has significantly greater amplitude compared to the negative control.

Figure 13A:
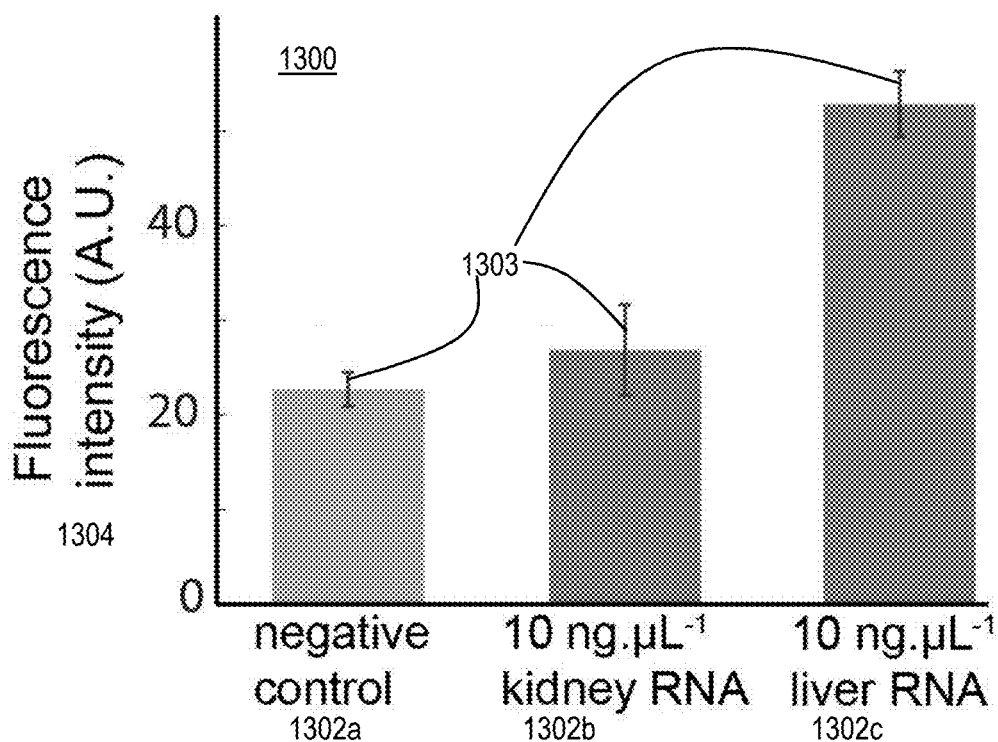
FIG. 13A is a graph that illustrates example demonstration of ITP hybridization assay for detection and quantification of miR-122 in kidney and liver, according to an embodiment.

FIG. 13A is a graph that illustrates example demonstration of ITP hybridization assay for detection and quantification of miR-122 in kidney and liver, according to an embodiment. The horizontal axis indicates three groups of results, for negative control 1302a, kidney RNA 1302b and liver RNA 1302c. The vertical axis 1324 indicates enhancement f Peak areas of ITP hybridization experiments are plotted where LEs initially contain 100 pM MB s targeting miR-122. The experiments shown have TEs which contain: a blank (left bar 1302a), 10 ng·μL$^{-1}$ of total RNA from human kidney (middle bar 1302b), and 10 ng·μL$^{-1}$ of total RNA from human liver (right bar 1302c). The increase in fluorescence for kidney over the control is not statistically significant, showing our assay predicts miR-122 concentration in kidney below a limit of detection of 3,000 copies per cell. The peak area for liver is significantly greater, indicating greater expression of miR-122. Uncertainty bars 1303 represent 95% confidence on the mean.

Figure 13B:
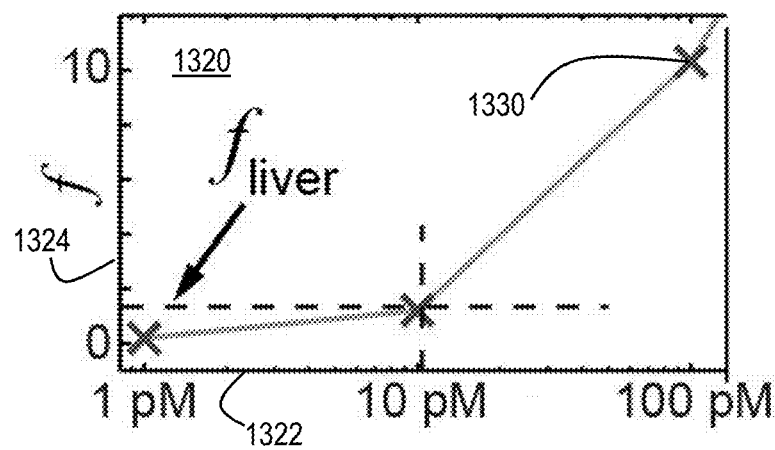
FIG. 13B is a graph that illustrates an example calibration curve resulting from interpolation of hybridization results from synthetic miR-122 as a function of concentration, according to an embodiment.

A calibration curve built using synthetic miR-122 is used to estimate target concentration from fluorescence enhancement. FIG. 13B is a graph that illustrates an example calibration curve resulting from interpolation of hybridization results from synthetic miR-122 as a function of concentration, according to an embodiment. The solid line shows a calibration curve resulting from interpolation of hybridization results from synthetic miR-122 versus concentration ("x" symbols 1330). This curve is used to calculate the concentration corresponding to the enhancement $f_{liver} = 1.3$. This concentration estimate is 10.3 pM, corresponding to approximately 16,000±400 copies per cell. Uncertainty bars represent 95% confidence on the mean.

These experimental embodiments showed that ITP hybridization enables length-selective detection of miRNA and can distinguish miRNA from its precursors. They also showed that the sequence specificity of MBs was unaffected by coupling hybridization with ITP. Furthermore, they demonstrated the efficacy of the assay for the detection of miRNA targets in total RNA. They successfully detected miR-122 in liver and corroborated reduced expression in kidney. Using calibration experiments, the amount of miR-122 in liver was calculated; and the estimate is in fair agreement with measurements performed with other quantification methods.

4.4 Use of Spacer Ions

Figure 14A:
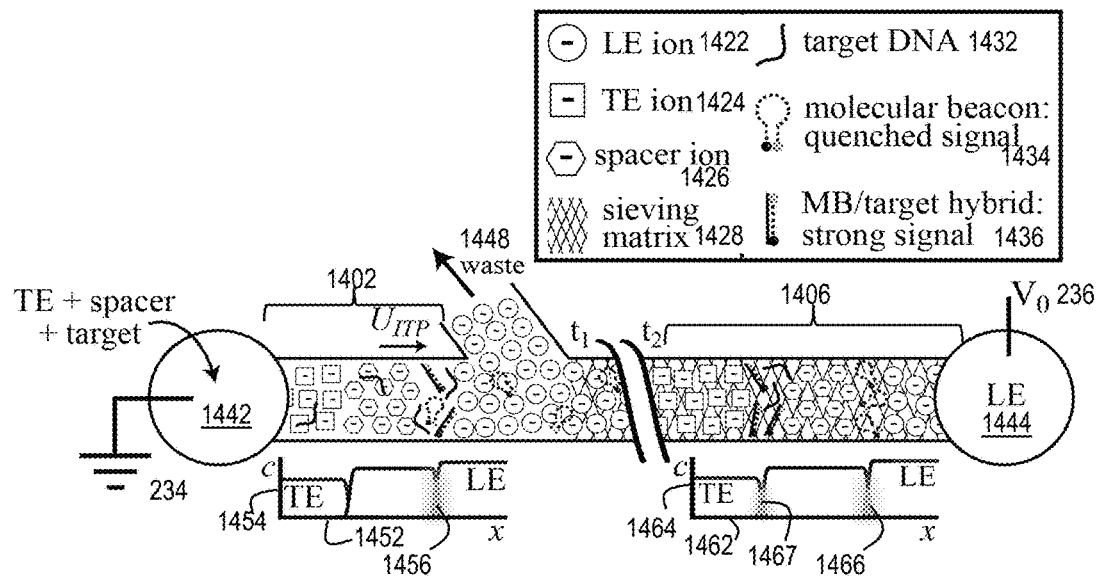
FIG. 14A is a block diagram that illustrates pre-concentration of the analyte and reporter ahead of a spacer ion in a first zone, and separation of bound and unbound reporter ions by the spacer ions using a higher concentration of one additive in a second zone, according to an embodiment.

In some embodiments, gel sieving matrix concentration gradients are used in ITP to first enhance reaction kinetics and then separate reactants in distinct focused zones, as shown in FIG. 14A. A spacer compound is added with mobility higher than that of the formed reactants but lower than that of the unreacted compounds within the gel matrix. As described above with reference to FIG. 4B, UV light is used to create a discrete gel region within a microchannel, thus partitioning the channel longitudinally into three separate regions. Molecular beacons and their complementary targets are used as example analytes. All analytes focus initially in free solution in peak mode at the spacer-LE interface. Upon entering the discrete gel region, the beacon-target complex mobility is reduced to below that of the spacer but not below that of the TE. The beacon mobility, however, remains bracketed by the LE and spacer. This enables separation of excess beacons from beacon-target hybrid, followed by refocusing of the beacon-target hybrid at the TE-spacer interface. Separation of excess beacon from beacon-target hybrid increases assay sensitivity by reducing the signal from imperfect quenching observed in other embodiments. This technique is demonstrated by enhancing the reaction between molecular beacons and a complementary 77nt precursor micro-RNA target in an 8% polyacrylamide gel matrix. The oligo sequences are given in Table 2. For this demonstration, miR-26a precursor was used as the target and miR-26a MB was used as the molecular beacon.

Figure 14B:
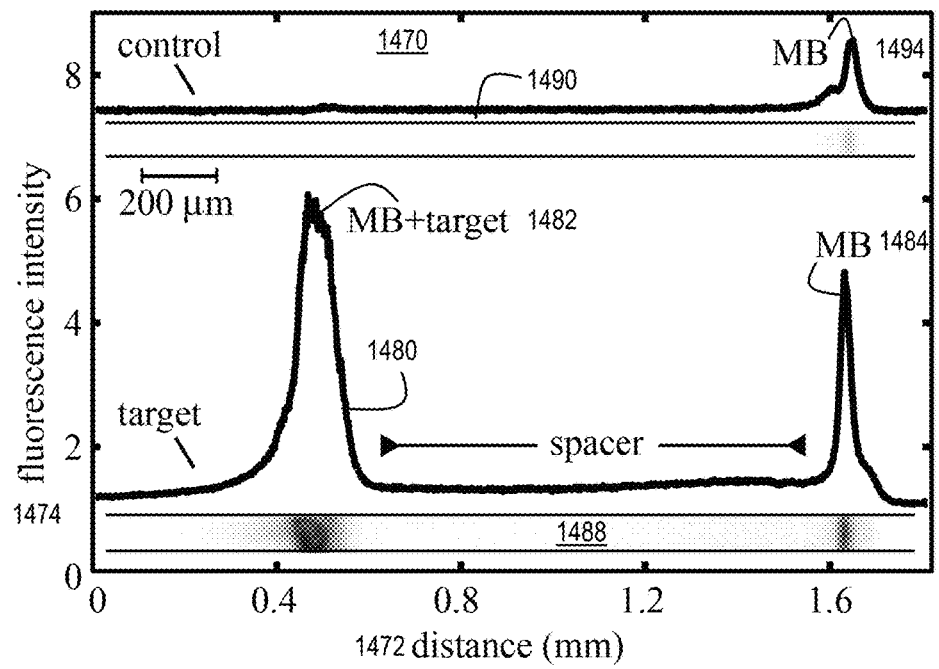
FIG. 14B is a graph that illustrates example measurements of bound and unbound reporter ions in the arrangements of FIG. 14A, according to an embodiment.

FIG. 14A is a block diagram that illustrates pre-concentration of the analyte and reporter ahead of a spacer ion in a first zone, and separation of bound and unbound reporter ions by the spacer ions using a higher concentration of one additive in a second zone, according to an embodiment. FIG. 14B depicts LE ions 1422, TE ions 1424, spacer ions 1426, target DNA ions 1432, molecular beacon ions 1434 and MB-target hybrid ions 1436, in each of the two zones 1402 and 1406. The TE spacer and target mixture at input port 1442 is at electrical ground 234 and the LE and MB mixture at output port 1444 is at a high voltage 236. In zone 1402 the target, spacer and MB begin to focus between the LE and TE. The MB, and target and hybrid product all have higher mobility than the spacer ion and thus focus between the spacer and LE as shown in the graph below with horizontal axis 1452 indicating distance along the channel and vertical axis 1454 indicating electrical field strength. The MB, target and MB-target hybrid are all focused at 1456, ahead of the spacer and behind the LE. In zone 1406, where the focus interface encounters the gel, the MB-target hybrid ions suffer reduced mobility and below that of the spacer ion and above that of the TE. The unbound target and MB, which are each half the size of the hybrid, retain mobilities greater than the spacer ion. This is reflected in the graph below with horizontal axis 1462 indicating distance along channel, vertical axis indicating electric field strength. The unbound target and MB are focused in interface 1466 between the spacer ions and LE. The MB-target hybrids are focused in the interface 1467 between the spacer ions and the TE.

This result is brought about by the following steps. During step 305, the channels are filled with a buffer that contains the leading electrolyte (LE), acrylamide/bisacrylamide monomer and cross-linker, and a photo-initiator. In this experiment the following were used: 50 mM Hydrochloric Acid (HCl) as LE, 100 mM Tris as a counte ion, 6% (w/v) acrylamide as monomer, 3.3% (w/w) bisacrylamide as cross-linker, and 0.2% (w/v) VA-086 as a photo-initiator. A mask is used to cover regions of the channel, allowing spatially-selective exposure to UV light, thus photo-patterning desired regions with high resolution. During step 311, a buffer containing the trailing electrolyte (TE), a spacer compound, and the analytes (in this case, a molecular beacon and its complementary target) is added to one of the wells, replacing the LE. SEQ. ID. NO 8 was used as synthetic oligoribonucleotides and SEQ. ID. NO. 9 was used as molecular beacon probes. During step 313, an electric field is applied using electrodes in the wells. ITP is thus carried out, focusing the analytes between the fast LE ions and the slow TE ions. The molecular beacon and its target will react, forming a complex, causing the stem-loop structure of the beacon to loosen and open, thus separating the fluorophore from its quencher, and increasing the fluorescence by nearly an order of magnitude. Free beacon, target, and beacon/target hybrid focus together at the spacer-LE interface. As the reactants enter the sieving matrix, the retarding effects of the gel reduce the mobility of the larger beacon-target complex below that of spacer ions. Unreacted beacons remain focused ahead of the spacer compound and beacon/target hybrid re-focuses at the TE-spacer interface.

FIG. 14B is a graph that illustrates example measurements of bound and unbound reporter ions in the arrangements of FIG. 14A, according to an embodiment. The horizontal axis 1472 is distance along the channel in mm. The vertical axis 1474 is fluorescence intensity in arbitrary units. In this experimental embodiment the target is a 77nt precursor micro-RNA. In the absence of target molecules trace 1490 results, displaced vertically about 6 units for clarity of presentation, shows molecular beacons focus primarily in one peak. The signal intensity band below trace 1490 shows weak fluorescent signal intensity due to the imperfect quenching of the fluorophore, and represents baseline intensity. In the presence of 1 μM precursor micro-RNA molecules trace 1480 results. Trace 1480 includes two peaks in the gel region, separated by the spacer ions, the latter peak being of significantly higher intensity, indicating the opening of the beacon, distancing the fluorophore from its quencher. The signal intensity band 1488 below trace 1480 shows strong fluorescent signal intensity at the latter peak. Inset images are taken from experiment visualizations.

4.5 Use of Reporter-Binding Agent Fixed in Polymer Gel

Spatial gradients of a modified gel capture matrix are used to first react target molecules and fluorescent reporters in ITP and then immobilize excess reporters, as shown in FIG. 15. This enables detection of target molecules, which remain bound to reporters. An acrylamide-modified probe is included with the monomer solution. This probe becomes incorporated into the polymers upon exposure to UV light and remains immobilized in the gel matrix. A discrete gel region containing capture probe is created within a microchannel, thus partitioning the channel axially into three regions.

Figure 15A:
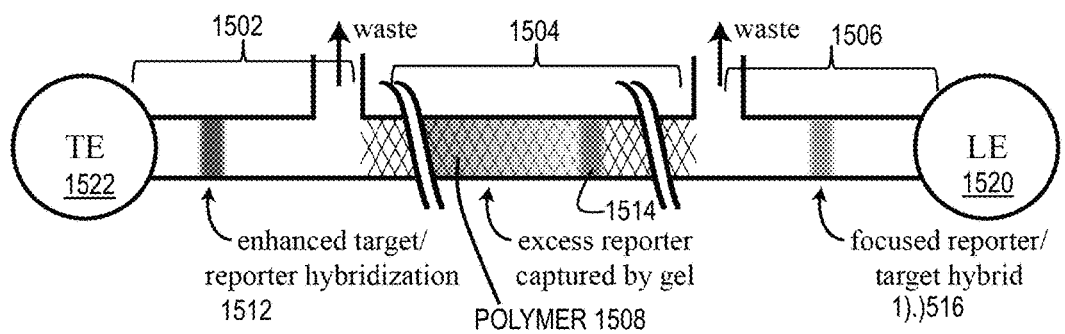
FIG. 15A is a block diagram that illustrates pre-concentration of the analyte and reporter, separation of bound and unbound reporter ions using a higher concentration of polymer sieve that fixes a reporter-binding probe in a second zone, and a third zone of only analyte-bound reporter ions in a third zone with no probe fixed in a polymer sieve, according to an embodiment.

FIG. 15A is a block diagram that illustrates pre-concentration of the analyte and reporter, separation of bound and unbound reporter ions using a higher concentration of polymer sieve that fixes a reporter-binding probe in a second zone, and third zone of only analyte-bound reporter ions in a third zone with no probe fixed in a polymer sieve, according to an embodiment. In the first zone 1502, target molecules are focused at interface 1512 and react with complementary reporter probes end-labeled with a fluorophore. In the second, gel-filled zone 1504, excess reporter probes become immobilized to the gel matrix 1508 via interaction (e.g. hybridization) with acrylamide-modified probes immobilized in the gel. Reporter probes bound to a target molecule remain focused at the ITP interface 1514 throughout this region as a result of slow off-rates. This enables detection of target molecules through visualization of the fluorescent reporter in the interface 1516 of the third zone 1506.

This technique is demonstrated by detecting target miR-15a molecules, using a complementary oligonucleotide capture probe modified with Acrydite, in a 4% polyacrylamide gel. The LE buffer is composed of 100 mM HCl, 200 mM Tris, and 2.5 mM MgCl. The channels are filled with LE buffer 1520, containing 10 μM acrylamide-modified (commercial name Acrydite-modified), 4% T 3% C acrylamide/ bisacrylamide monomer and crosslinker 1% PVP (MW 1,000,000), and 0.13% VA-086 photoinitiator. A mask is used to photo-pattern desired regions of the channel. Electric field is applied using electrodes in the wells to remove unincorporated capture probe away from the capture region. A TE buffer 1522 containing a fluorescent reporter and target molecules is added to one of the wells, replacing the LE. The sequences of synthetic oligoribonucleotides and probes used in this work are listed in Table 3. Electric field is applied using electrodes in the wells. ITP is thus carried out, focusing the analytes between the fast LE ions and the slow TE ions. The reporter probes and complementary target molecules initially react in free solution, forming a target/ reporter hybrid. As the ITP interface enters the gel region, excess reporters hybridize with the immobilized complementary oligonucleotides and therefore become immobilized in the gel matrix. Due to low off-rates, the target/ reporter complex remains hybridized throughout the gel region. The fluorescent signal is measured in the third (free solution) region. Signal intensity is proportional to initial concentration of target molecules.

TABLE 3

Nucleic acids used in reporter-binding agent experiments

| Oligo name (length) | SEQ. ID. NO | Sequence (5' to 3') |
|---|---|---|
| miR-15a (22 nt) | 11 | UAGCAGCACAUAAUGGUUUGUG |
| miR-15a Probe (23 nt) | 12 | Acrydite-GTAGCAGCACATAA TGGTTTGTG |
| miR-15a Reporter (23 nt) | 13 | Cy3-CACAAACCATTATGT GCTGCTA |

Figure 15B:
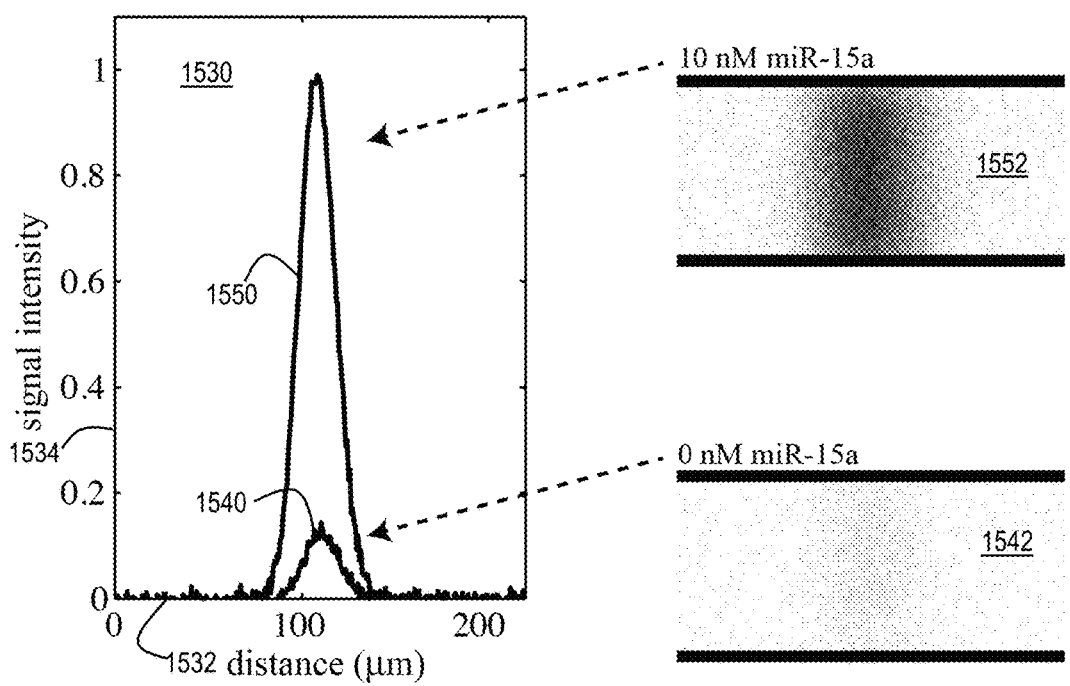
FIG. 15B is a graph that illustrates example measurements of analyte-bound control in the arrangements of FIG. 15A, according to an embodiment.

FIG. 15B is a graph that illustrates example measurements of analyte-bound control in the arrangements of FIG. 15A, according to an embodiment. The horizontal axis 1532 is distance along the channel at the viewing point. The vertical axis 1534 is fluorescence signal intensity in arbitrary units. In the detection of miR-15a, a 10 μM acrylamide-modified oligonucleotides and 10 nM fluorescent reporter are used. In the presence of zero target molecules indicated by trace 1540 and image 1542, reporter probes become immobilized in the gel capture matrix. This results in a weak fluorescence signal. In the presence of 10 nM target molecules (miR-15a) indicated by trace 1550 and image 1552, fluorescent reporters hybridize to target molecules and thus remain focused in ITP. This results in a strong fluorescence signal.

5. Alternative Embodiments

In alternative embodiments, one or more analytes, reporters or product molecules include one or more of the sequences described in this section.

It is known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," is known in the art to refer to the region between the translation initiation codon and the translation termination codon. It is also known in the art that variants can be produced through the use of alternative signals to start or stop transcription and that pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

In the context of various embodiments, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides that can hydrogen bond with each other. Thus, "specifically hybridizable" and "complementary" are terms that are used to indicate a sufficient degree of complementarity or precise pairing such that stable and specific binding occurs between the nucleic acid and the DNA or RNA target.

Various conditions of stringency can be used for hybridization as is described below. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1 6.3.6, which is incorporated by reference. Aqueous and nonaqueous methods are described in that reference and either can be used. Specific hybridization conditions referred to herein are as follows: 1) low stringency hybridization conditions in 6.times.sodium chloride/ sodium citrate (SSC) at about 45° C., followed by two washes in 0.2.times.SSC, 0.1% SDS at least at 50.degree C. (the temperature of the washes can be increased to 55° C. for low stringency conditions); 2) medium stringency hybridization conditions in 6.times.SSC at about 45° C., followed by one or more washes in 0.2.times.SSC, 0.1% SDS at 60° C.; 3) high stringency hybridization conditions in 6.times.SSC at about 45° C., followed by one or more washes in 0.2.times.SSC, 0.1% SDS at 65° C.; and preferably 4) very high stringency hybridization conditions are 0.5M sodium phosphate, 7% SDS at 65° C., followed by one or more washes at 0.2.times.SSC, 1% SDS at 65° C. Very high stringency conditions (4) are the preferred conditions and the ones that should be used unless otherwise specified.

Nucleic acids in the context of various embodiments include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. DNA/RNA chimeras are also included.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure; however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Oligonucleotides containing modified backbones or non-natural internucleoside linkages can be used. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkyl-phosphotriesters, methyl and other alkyl phosphonates including 3-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference. Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In some oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Some embodiments of some embodiments use oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene(methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_{n}NH_2$, $O(CH_2)_nCH_3$, $O(CH_2)_nONH_2$, and $O(CH_2)_nON[(CH_2)_{n}CH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy(2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethylamino-ethoxyethyl or 2'-DMAEOE), i.e., 2'-O—$CH_2$—O—$CH_2$—N($CH_3$)$_2$, also described in examples hereinbelow.

A further modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other modifications include 2'-methoxy(2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro(2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C.ident.C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of some embodiments. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides for use in some embodiments involves chemically linking to the oligonucleotide one or more moieties or conjugates which enhance the activity, cellular distribution or cellular uptake of the oligonucleotide. The compounds of some embodiments can include conjugate groups covalently bound to functional groups such as primary or secondary hydroxyl groups. Conjugate groups of some embodiments include intercalators, reporter molecules, polyamines, polyamides, poly ethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of various embodiments, include groups that improve oligomer uptake, enhance oligomer resistance to degradation, and/or strengthen sequence-specific hybridization with RNA. Groups that enhance the pharmacokinetic properties, in the context of various embodiments, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et. al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid; e.g., di hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937. Oligonucleotides of some embodiments may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. "Chimeric" compounds or "chimeras," in the context of various embodiments, are oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids.

The oligonucleotides used in accordance with various embodiments may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. An isotachophoresis method comprising:
    (a) forming a concentration gradient of a matrix material along a channel, wherein the channel connects an input port to an output port, and wherein the input port is configured to receive a sample comprising an analyte;
    (b) introducing ions into the channel, wherein the ions comprise
        (i) a leading electrolyte having a first effective mobility magnitude greater than an effective mobility magnitude of the analyte, and
        (ii) a trailing electrolyte having a second effective mobility magnitude less than the effective mobility magnitude of the analyte;
    (c) contacting the analyte to the leading electrolyte;
    (d) contacting the trailing electrolyte to the analyte; and
    (e) applying an electric field to the channel,
    wherein the matrix material affects at least one of the analyte, the leading electrolyte or the trailing electrolyte in at least a portion of the channel.

2. The method of claim 1, wherein the matrix material comprises a stationary material.

3. The method of claim 2, wherein the matrix material comprises a stationary polymeric material.

4. The method of claim 1, wherein the matrix material is ion permeable.

5. The method of claim 1, further comprising detecting the analyte.

6. The method of claim 1, wherein the analyte is a protein.

7. The method of claim 1, wherein the analyte is a nucleic acid.

8. The method of claim 1, further comprising introducing an additional ion into the channel via an additional channel at a junction, wherein the additional ion is different from the leading electrolye, the trailing electrolye, and the analyte.

9. The method of claim 8, wherein prior to the introducing the additional ion, the additional ion is substantially absent from the channel.

10. The method of claim 8, wherein the additional ion comprises a weak base or a weak acid.

11. The method of claim 8, wherein the introducing the additional ion is conducted after the analyte has migrated along the channel at least to the junction.

12. The method of claim 8, wherein the introducing the additional ion is triggered by a feedback signal.

13. The method of claim 12, wherein the feedback signal is triggered by detection of an optical signal or an electrical signal.

14. An apparatus comprising:
    (a) a channel connecting an input port to an output port, wherein the input port is configured to receive a sample comprising an analyte;
    (b) a concentration gradient of a matrix material located in the channel;
    (c) a leading electrolyte, wherein the leading electrolyte has a first effective mobility magnitude greater than an effective mobility magnitude of the analyte;
    (d) a trailing electrolyte, wherein the trailing electrolyte has a second effective mobility magnitude less than the effective mobility magnitude of the analyte; and
    (e) an electric field generator capable of applying an electric field to the channel,
    wherein the matrix material affects at least one of the analyte, the leading electrolyte or the trailing electrolyte in at least a portion of the channel.

15. The apparatus of claim 14, wherein the matrix material comprises a stationary material.

16. The apparatus of claim 15, wherein the matrix material comprises a stationary polymeric material.

17. The apparatus of claim 14, wherein the matrix material is ion permeable.

18. The apparatus of claim 14, wherein the matrix material is functionalized with at least one type of capture molecule.

19. The apparatus of claim 14, wherein the apparatus further comprises a detector.

20. The apparatus of claim 14, wherein the analyte is a protein.

21. The apparatus of claim 14, wherein the analyte is a nucleic acid.

22. The apparatus of claim 14, further comprising an additional channel connected to the channel.

23. The apparatus of claim 22, further comprising an additional ion in the additional channel.

24. The apparatus of claim 22, wherein the additional channel comprises a side channel connected to the channel at a junction and wherein the electric field generator is configured to apply an electric field to the side channel when the analyte migrates through the channel to the junction.

25. The apparatus of claim 23, wherein the additional ion comprises a weak base or a weak acid.

26. The apparatus of claim 23, wherein the additional ion is not present in the channel.

27. The apparatus of claim 24, wherein the application of the electric field to the side channel is activated by a feedback signal.

28. The apparatus of claim 24, wherein the feedback signal is triggered by detection of an optical signal or an electrical signal.

29. An isotachophoresis method comprising:
    (a) forming a concentration gradient of a matrix material along a channel, wherein the channel connects an input port to an output port, and wherein the input port is configured to receive a sample comprising an analyte;
    (b) introducing ions into the channel, wherein the ions comprise
        (i) a leading electrolyte having a first effective mobility magnitude greater than an effective mobility magnitude of the analyte, and
        (ii) a trailing electrolyte having a second effective mobility magnitude less than the effective mobility magnitude of the analyte;
    (c) contacting the analyte to the leading electrolyte;
    (d) contacting the trailing electrolyte to the analyte; and
    (e) applying an electric field to the channel, wherein the matrix material is functionalized with specific capture molecules.

30. The method of claim 29, wherein the specific capture molecules are present in a concentration gradient along the channel.

31. The method of claim 29, wherein the specific capture molecules comprise at least one of the group consisting of a macromolecule, a nucleic acid, an antibody, an antigen, biotin, avidin, a ligand, a receptor, a bait molecule, and a protein.

32. An isotachophoresis method comprising:
(a) forming a concentration gradient of a matrix material along a channel, wherein the channel connects an input port to an output port, and wherein the input port is configured to receive a sample comprising an analyte;
(b) introducing ions into the channel, wherein the ions comprise
   (i) a leading electrolyte having a first effective mobility magnitude greater than an effective mobility magnitude of the analyte, and
   (ii) a trailing electrolyte having a second effective mobility magnitude less than the effective mobility magnitude of the analyte;
(c) contacting the analyte to the leading electrolyte; and
(d) contacting the trailing electrolyte to the analyte; and
   (e) applying an electric field to the channel,
wherein the matrix material is functionalized with probe molecules.

* * * * *